United States Patent
Kobilka et al.

(10) Patent No.: US 10,590,152 B2
(45) Date of Patent: Mar. 17, 2020

(54) PINENE-BASED FLAME RETARDANT COMPOUNDS

(71) Applicant: International Business Machines Corporation, Armonk, NY (US)

(72) Inventors: Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 90 days.

(21) Appl. No.: 15/842,356

(22) Filed: Dec. 14, 2017

(65) Prior Publication Data

US 2019/0185497 A1 Jun. 20, 2019

(51) Int. Cl.

| | |
|---|---|
| *C07F 9/32* | (2006.01) |
| *C07F 9/40* | (2006.01) |
| *C07F 9/655* | (2006.01) |
| *C08K 5/5373* | (2006.01) |
| *C08K 5/5357* | (2006.01) |
| *C08K 5/5313* | (2006.01) |
| *C08J 3/20* | (2006.01) |
| *C08G 79/04* | (2006.01) |
| *C08G 59/30* | (2006.01) |
| *C08G 65/22* | (2006.01) |
| *C08K 5/00* | (2006.01) |

(52) U.S. Cl.
CPC .......... *C07F 9/3276* (2013.01); *C07F 9/3282* (2013.01); *C07F 9/4081* (2013.01); *C07F 9/4084* (2013.01); *C07F 9/65502* (2013.01); *C07F 9/65505* (2013.01); *C08G 59/304* (2013.01); *C08G 65/22* (2013.01); *C08G 79/04* (2013.01); *C08J 3/203* (2013.01); *C08K 5/5313* (2013.01); *C08K 5/5357* (2013.01); *C08K 5/5373* (2013.01); *C08J 2385/02* (2013.01); *C08K 5/0066* (2013.01)

(58) Field of Classification Search
CPC .... C07F 9/3276; C07F 9/3282; C07F 9/4081; C07F 9/4084; C07F 9/65502; C07F 9/65505

See application file for complete search history.

(56) References Cited

U.S. PATENT DOCUMENTS

| 6,271,408 B1 | 8/2001 | Pfander et al. |
| 2006/0063867 A1 | 3/2006 | Durairaj et al. |
| 2017/0044282 A1 | 2/2017 | Howdle et al. |

FOREIGN PATENT DOCUMENTS

| CN | 104194574 A | 12/2014 |
| EP | 0911311 A1 | 4/1999 |
| WO | 2004016712 A1 | 2/2004 |

OTHER PUBLICATIONS

"Researchers Develop Pinene-based Plastic: University of Bath," SpecialChem News, Jan. 13, 2017, pp. 1-2. http://specialchem4bio.com/news/2017/01/13/researchers-develop-pinene-based-plastic-university-of-bath?Ir=SC4BNL170199&li=#utm_source=NL&utm_medium=EML&utm_campaign=SC4BNL170199.

Quilter et al., "Polymerisation of a terpene-derived lactone: a bio-based alternative to ε-caprolactone," Polymer Chemistry, Dec. 2016, 8(5), pp. 833-837, The Royal Society of Chemistry. http://dx.doi.org/10.1039/C6PY02033J.

Traber et al., "Facile synthesis of the cyclopentane moiety of (all-E,2R,5R,6S)-2,6-cyclolycopene-1,5-diol," Tetrahedron Letters, 2000, pp. 7197-7198, Elsevier Science Ltd.

SciFinder search results for synthesis of phosphorus-containing compounds, received: Oct. 27, 2017, 2 pages.

*Primary Examiner* — Edward J Cain

(74) *Attorney, Agent, or Firm* — Kelsey M. Skodje

(57) ABSTRACT

A pinene-based flame retardant compound, a process for forming a flame retardant polymer, and an article of manufacture comprising a material that contains a pinene-based flame retardant polymer are disclosed. The pinene-based flame retardant compound includes a pinene derivative core and at least one flame retardant substituent having a phosphorus-based moiety. The process for forming the flame retardant polymer includes obtaining pinene, forming a derivative of pinene, obtaining a phosphorus-based compound, reacting the phosphorus-based compound and the pinene derivative to form a pinene-based flame retardant compound, and incorporating the pinene-based flame retardant compound into a polymer to form the pinene-based flame retardant polymer.

7 Claims, 21 Drawing Sheets

350

352   3-Mercaptopropionate 356   2-Mercaptoethanol

360   Cysteamine HCl 500-5

TBSCl,
Imidazole, DCM

404

524 dil. H⁺

544

1. 204, Et₃N, DCM
2. Deprotection
3. 206, Et₃N, DCM

548

500-6

408

↓ Cs₂CO₃, 208 or 210, DMF 552    or    556

600-2

R$^1$ =

306

PINENE-BASED FLAME RETARDANT COMPOUNDS

BACKGROUND

The present disclosure relates to bio-renewable flame retardant compounds and more specifically to pinene-based flame retardant compounds.

Bio-based, sustainable compounds can be used in applications and syntheses of compounds that previously required petroleum-based raw materials. For example, bio-based compounds can be building blocks for plastics, adhesives, pharmaceuticals, etc. There are numerous strategies for efficiently and inexpensively producing bio-based polymers on an industrial scale. Examples of these strategies can be found in fermentation technologies, membrane technologies, and genetic engineering. Alpha ($\alpha$)-pinene (2,6,6-trimethylbicyclo[3.1.1]hept-2-ene) and beta ($\beta$)-pinene ((1S, 5S)-6,6-dimethyl-2-methylenebicyclo[3.1.1]heptane) are examples of bio-based compounds. $\alpha$- and $\beta$-pinene are obtained from sources that can include pine resin, turpentine, sage, etc.

SUMMARY

Various embodiments are directed to pinene-based flame retardant compounds. The pinene-based flame retardant compounds have pinene derivative cores and one or more flame retardant substituents. The flame retardant substituents have phosphorus-based moieties, such as phosphoryl or phosphonyl moieties. The flame-retardant substituents can have phenyl groups and functional groups such as allyl groups, epoxy groups, propylene carbonate groups, amino groups, carboxylic acid groups, and hydroxyl groups. Additionally, the flame-retardant substituents can have thioether-linked groups. The pinene-based flame retardant compounds can be formed from pinene obtained from a bio-based source.

Additional embodiments are directed to a process of forming a pinene-based flame retardant polymer. The pinene-based flame retardant polymer can be produced by obtaining pinene, forming a pinene derivative, obtaining a phosphorus-based compound, reacting the phosphorus-based compound and the pinene to form a pinene-based flame retardant compound, and incorporating the pinene-based flame retardant compound into a polymer to form the flame retardant polymer. The pinene can come from a bio-based source. The phosphorus-based compound can be a phosphorus-based compound with allyl, epoxy, and/or phenyl groups. The pinene-based flame retardant compound can have at least one functional group such as an allyl group, an epoxy group, a propylene carbonate group, a carboxylic acid group, an amine group, or a hydroxyl group. The pinene-based flame retardant compound can be incorporated into the polymer by blending, binding, or polymerizing.

Further embodiments are directed to an article of manufacture comprising a material that contains a pinene-based flame retardant polymer. The article of manufacture can also contain an electronic component. Additionally, the material containing the pinene-based flame retardant polymer can be a plastic for integrated circuit packing or an adhesive. The pinene-based flame retardant polymer can also be combined with an additive such as a cross-linker, a chain-extender, a blowing agent, an inorganic pigment, an organic pigment, a flame retardant, a surfactant, a filler, a smoke suppressant, and a plasticizer.

DETAILED DESCRIPTION

Figure 1:
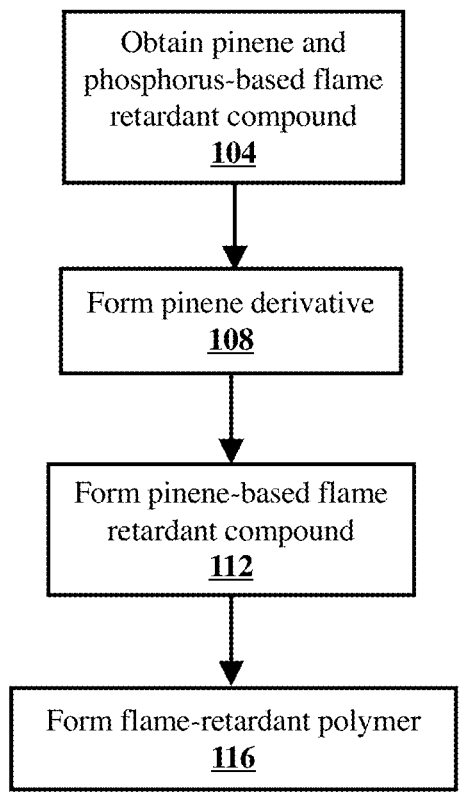
FIG. 1 is a flow diagram illustrating a process of forming a flame retardant polymer containing a pinene-based flame retardant polymer.

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies can be found in fermentation technologies, membrane technologies, and genetic engineering. Biotechnological strategies can include plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of uses for bio-based compounds include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can impart flame retardant properties to bio- and petroleum-based polymers. For example, flame retardant compounds or cross-linkers can be incorporated into polymers. Additionally, flame retardant monomers can be polymerized to form flame retardant polymers.

Pinene is one example of a bio-based compound that can have applications as a component of various polymers, resins, and monomers. Pinene can be obtained from conifer (e.g., pine) resin, as well as numerous other plants. Examples of plants that contain pinene include *Heterotheca, Artemisia tridentata, Sideritis, Salvia, Cannabis, Pistacia terebinthus, Cuminum cyminum, Humulus lupulus, Pinus pinaster, Clausena anisata*, etc. There are two isomers of pinene, alpha ($\alpha$)-pinene (2,6,6-trimethylbicyclo[3.1.1]hept-2-ene) and beta ($\beta$)-pinene ((1S, 5S)-6,6-dimethyl-2-methylenebicyclo[3.1.1]heptane). These two isomers can be converted into one another via isomerization reactions.

According to the present disclosure, pinene is used as a precursor for flame retardant compounds. These compounds can include small molecules, cross-linkers, monofunctional molecules, and monomers, which are polymerized to form flame retardant polymers. The pinene-based flame retardant small molecules can be added to polymers, fabrics, resins, or other materials during blending, curing, foaming, extrusion, or other processing techniques, and the pinene-based cross-linkers and monofunctional molecules can be bound to polymer chains at one or more active sites. In addition to directly adding the pinene-based flame retardant compounds to the materials during processing, the added pinene-based flame retardant compounds can be contained within microcapsules.

FIG. 1 is a flow diagram illustrating a process 100 of forming a flame retardant polymer containing a pinene-based flame retardant polymer. Process 100 begins with the obtainment of pinene and a phosphorus-based compound. This is illustrated at step 104. The phosphorus-based compounds provide flame retardant groups to the pinene derivatives in subsequent steps. Each phosphorus-based compound has either a phosphoryl or a phosphonyl moiety (collectively referred to as an FR group) with a phenyl (Ph) or other alkyl substituent and a functional group or second phenyl/alkyl substituent. The functional groups are reactive groups involved in polymerization or binding to polymer chains. These functional groups can vary, as is discussed in greater detail below. The phosphorus-based compounds can be phosphate- or phosphonate-based compounds. The phosphorus-based compounds can be synthesized as needed, or obtained from a commercial source. The structures and syntheses of phosphorus-based compounds are discussed in greater detail with respect to FIGS. 2, 3A, and 3B.

Additionally, pinene is obtained from a bio-based source, such as a resin (e.g., conifer resin) or turpentine. Examples of plants that contain pinene include *Heterotheca, Artemisia tridentata, Sideritis, Salvia, Cannabis, Pistacia terebinthus, Cuminum cyminum, Humulus lupulus, Pinus pinaster, Clausena anisata*, etc. Pinene is isolated as $\alpha$-pinene, $\beta$-pinene, or a combination of the two. Further, $\alpha$- and $\beta$-pinene can be converted into one another via isomerization reactions.

Process 100 continues with the formation of a pinene derivative. This is illustrated at step 108. The isomer of pinene that is obtained in step 104 determines the identities of pinene derivatives and pinene-based flame retardant compounds produced in subsequent syntheses. The syntheses of pinene-derivatives are discussed in greater detail with respect to FIGS. 4A and 4B. It should be noted that the formation of the pinene derivative in step 108 is illustrated as occurring after the formation of the phosphorus-based compound in step 104. However, in some embodiments, step 108 occurs before step 104. Further, steps 104 and 108 can be carried out simultaneously in some embodiments.

The pinene derivative and the phosphorus-based compound are reacted to form a pinene-based flame retardant compound. This is illustrated at step 112. The identity of the pinene-based flame retardant compound is determined by the reaction conditions and the identities of the pinene derivatives and the phosphorus-based compounds used in the reaction. The FR groups of the phosphorus-based compounds are bonded at the locations of hydroxyl or chloride groups on the pinene derivatives in the reaction. Additionally, in some embodiments, modifications to the FR groups (e.g., forming or attaching new functional groups) are made after binding to the pinene derivative. The syntheses and structures of pinene-based flame retardant compounds are discussed in greater detail with respect to FIGS. 5A-5G and 6A-6C.

The pinene-based flame retardant compound formed in step 112 is incorporated into a polymer, either by blending, binding, or polymerization, yielding a pinene-based flame retardant polymer. This is illustrated at step 116. The pinene-based flame retardant compounds can be added to a polymer as small molecules, cross-linkers, or bound monofunctional molecules. This addition can involve chemical crosslinking, mixing, blending, forming a matrix, forming a composite polymer, etc. The addition of the pinene-based flame retardant compounds to the polymers can also occur without binding to the polymer during blending, curing, foaming, extrusion, or other processing techniques. Further, the pinene-based flame retardant compounds can be polymerized in a reaction with a base and/or a second monomer. Additionally, the pinene-based flame retardant compound can self-polymerize, or be polymerized in a reaction with a Ziegler-Natta catalyst. Polymerization reactions with the pinene-based flame retardant compounds are discussed in greater detail with respect to FIG. 7B.

Figure 2:
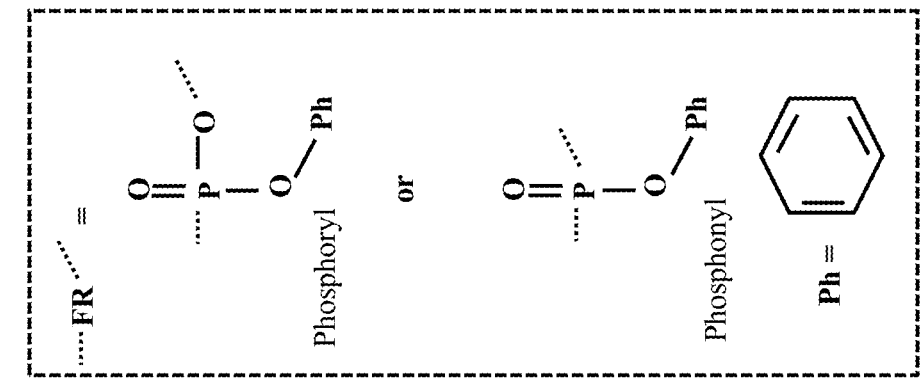
FIG. 2 is a diagrammatic representation of the molecular structures of functionalized phosphorus-based compounds, as well as phenyl-substituted phosphorus-based compounds, according to some embodiments of the present disclosure.
Figure 2:
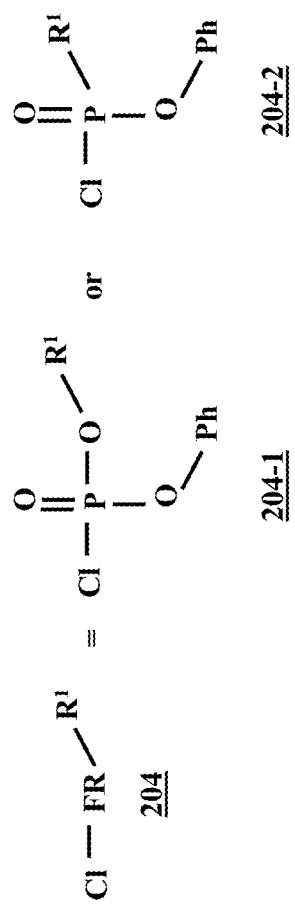
Figure 2:
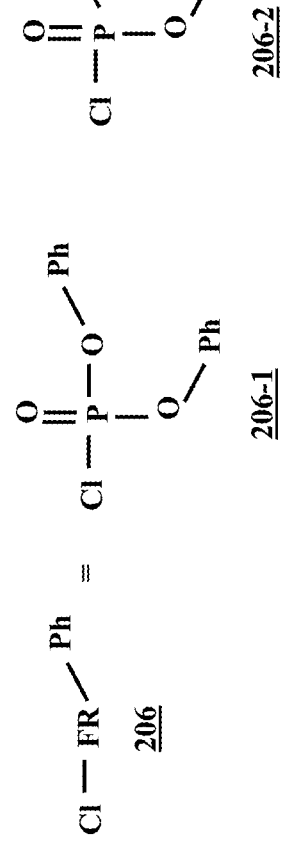
Figure 2:
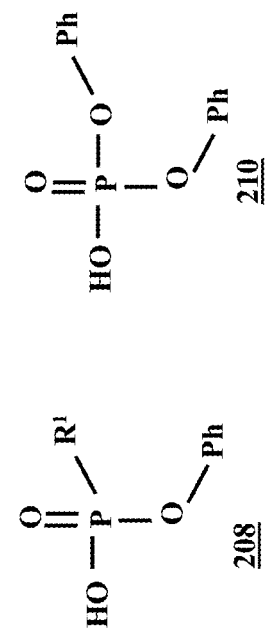

FIG. 2 is a diagrammatic representation of the molecular structures 200 of functionalized phosphorus-based compounds 204-1 and 204-2 (referred to collectively as 204) and 210, as well as phenyl-substituted phosphorus-based compounds 206-1 and 206-2 (referred to collectively as 206) and 208, according to some embodiments of the present disclosure. Each phosphorus-based compound is either a phosphate-based compound 204-1, 206-1, and 210 or a phosphonate-based compound 204-2, 206-2, and 208. These phosphonate compounds provide flame retardant substituents to the pinene derivatives. In order to simplify illustrations of the molecular structures, phosphoryl and phosphonyl moieties in the phosphate- and phosphonate-based compounds, respectively, are replaced by the abbreviation "FR".

The compounds referred to as phenyl-substituted phosphorus-based compounds 206 and 210 each have two phenyl (Ph) substituents. The compounds referred to as $R^1$-functionalized phosphorus-based compounds 204 and 208 each have an $R^1$ functional group in addition to a single phenyl (Ph) substituent. In some embodiments, the at least one phenyl substituent is replaced by another alkyl substituent (e.g., methyl, ethyl, propyl, isopropyl, etc.). Example syntheses of the $R^1$-functionalized phosphorus-based compounds 204 and 208, as well as examples of $R^1$ functional groups, are discussed with respect to FIGS. 3A and 3B. The phosphorus-based compounds 204, 210, 206, and 208 are reacted with pinene derivatives to form pinene-based flame retardant compounds. In some embodiments, modifications to the $R^1$ groups are made in additional reactions, which are carried out after the phosphorus-based compounds 204, 206, 210, and 208 are bound to the pinene derivative. These modifications can replace the $R^1$ functional groups with alternative functional groups or substituents. This is discussed in greater detail below.

Herein, pinene-based flame retardant compounds are referred to as functionalized (e.g., $R^1$-functionalized) or phenyl-substituted. Terminal functional groups attached to FR moieties (e.g., allyl, epoxy, propylene carbonate, amino, carboxylic acid, and hydroxyl groups) are involved in binding to polymer chains and/or polymerization reactions, while the phenyl substituents on the FR moieties do not participate in these reactions. Therefore, any pinene-based flame retardant compound with at least one functional group is referred to as functionalized to indicate that the compound will participate in binding or polymerization. Pinene-based flame retardant compounds with only phenyl or other alkyl substituents on their FR moieties act as small molecules that cause a polymer to be flame retardant when blended into the polymer.

The processes of forming the pinene-based flame retardant compounds illustrated herein can be carried out with different combinations of phosphorus-based compounds 204 and 206. In some embodiments, these processes can be carried out with either all phosphate-based compounds (204-1 and/or 206-1) or all phosphonate-based compounds (204-2 and/or 206-2). In other embodiments, a mixture of both phosphate- and phosphonate-based compounds can be used. Carrying out these processes with a mixture of phosphate- and phosphonate-based compounds (206-1/206-2 and/or 204-1/204-2) can result in the production of pinene-based flame retardant monomers with both phosphoryl and phosphonyl FR groups.

However, in some instances, adding a mixture of phosphate- and phosphonate-based compounds (206-1/206-2 or 204-1/204-2) can result in the production of pinene-based flame retardant monomers with all phosphoryl or all phosphonyl FR moieties. Additionally, adding a mixture of phosphate- and phosphonate-based compounds (206-1/206-2 or 204-1/204-2) to the reaction can yield a mixture of products that includes some combination of pinene-based flame retardant monomers with either all phosphoryl or all phosphonyl FR groups and pinene-based flame retardant monomers with both phosphoryl and phosphonyl FR groups.

Figure 3A:
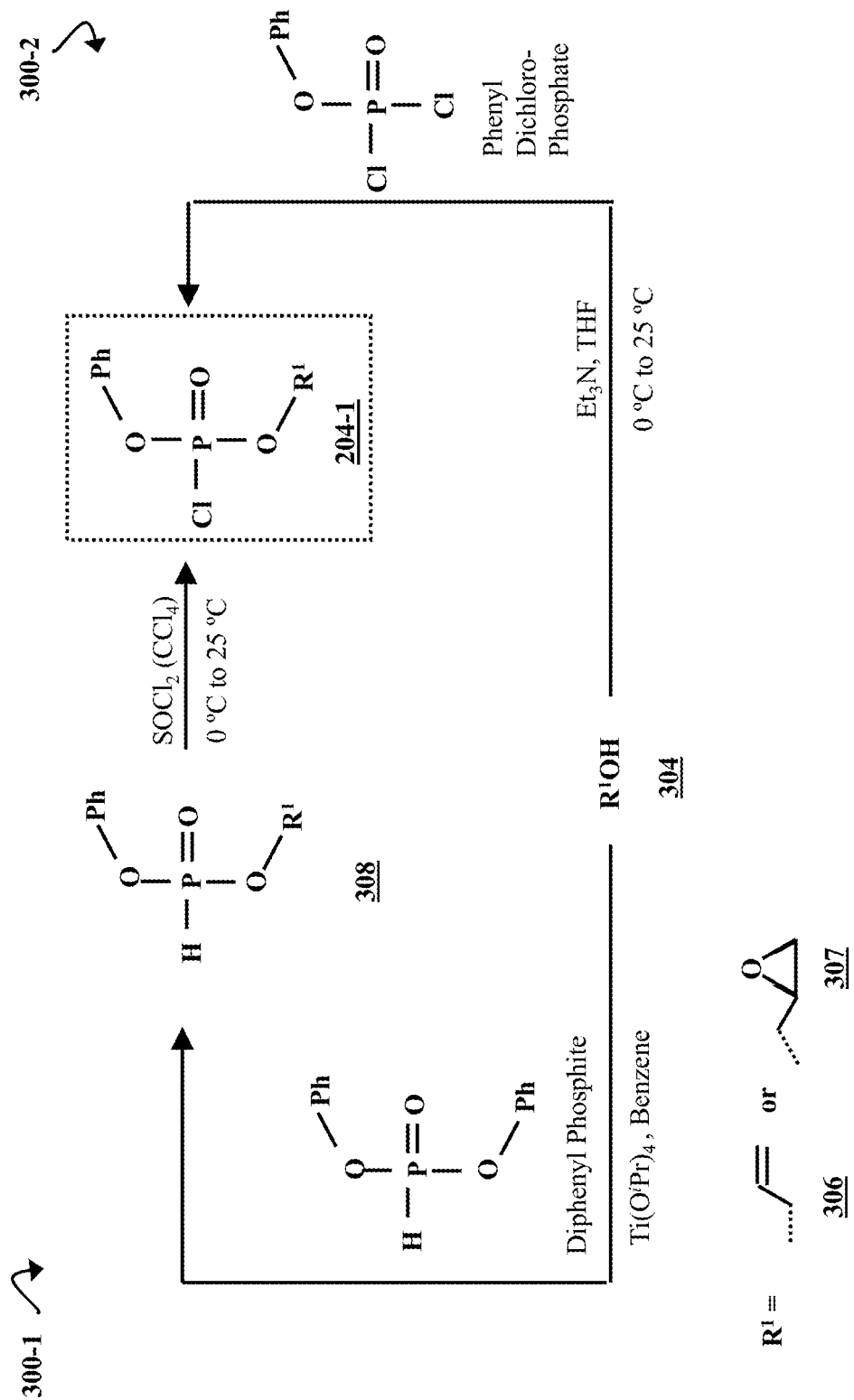
FIG. 3A is a chemical reaction diagram illustrating two processes of forming an $R^1$-functionalized phosphate-based compound, according to some embodiments of the present disclosure.

FIG. 3A is a chemical reaction diagram illustrating two processes 300-1 and 300-2 of forming an $R^1$-functionalized phosphate-based compound 204-1, according to some embodiments of the present disclosure. In both processes 300-1 and 300-2, an alcohol ($R^1OH$) 304 is a starting material for the $R^1$-functionalized phosphate-based compound 204-1. The alcohol 304 has either an allyl $R^1$ group 306 or an epoxy $R^1$ group 307. It should be noted that, though $R^1$ groups with single methylene bridge groups are illustrated here, other alcohols with chains of varying lengths (e.g., one to twelve methylene bridge groups) could be used. Additionally, alcohols with acrylate substituents are used in some embodiments.

In process 300-1, the alcohol 304 is reacted with diphenyl phosphite and titanium isopropoxide ($Ti(O^iPr)_4$) in benzene to produce a precursor 308 to the $R^1$-functionalized phosphate-based compound 204-1. In this pseudo-transesterification reaction, the precursor 308 is formed when a phenyl (Ph) substituent on diphenyl phosphite is replaced by the $R^1$ group from the alcohol 304. The precursor 308 is then reacted with thionyl chloride ($SOCl_2$) and carbon tetrachloride ($CCl_4$) over a range of approximately 0° C. to room temperature (RT, e.g., 15-27° C.), forming the $R^1$-functionalized phosphate-based compound 204-1.

In process 300-2, the alcohol 304 is reacted with phenyl dichlorophosphate in a tetrahydrofuran (THF) solution containing triethylamine ($Et_3N$). This process is carried out over a range of approximately 0° C. to room temperature (RT, e.g., 15-27° C.). A chloride on the phenyl dichlorophosphate is replaced by the alcohol 304, forming the $R^1$-functionalized phosphate-based compound 204-1.

Figure 3B:
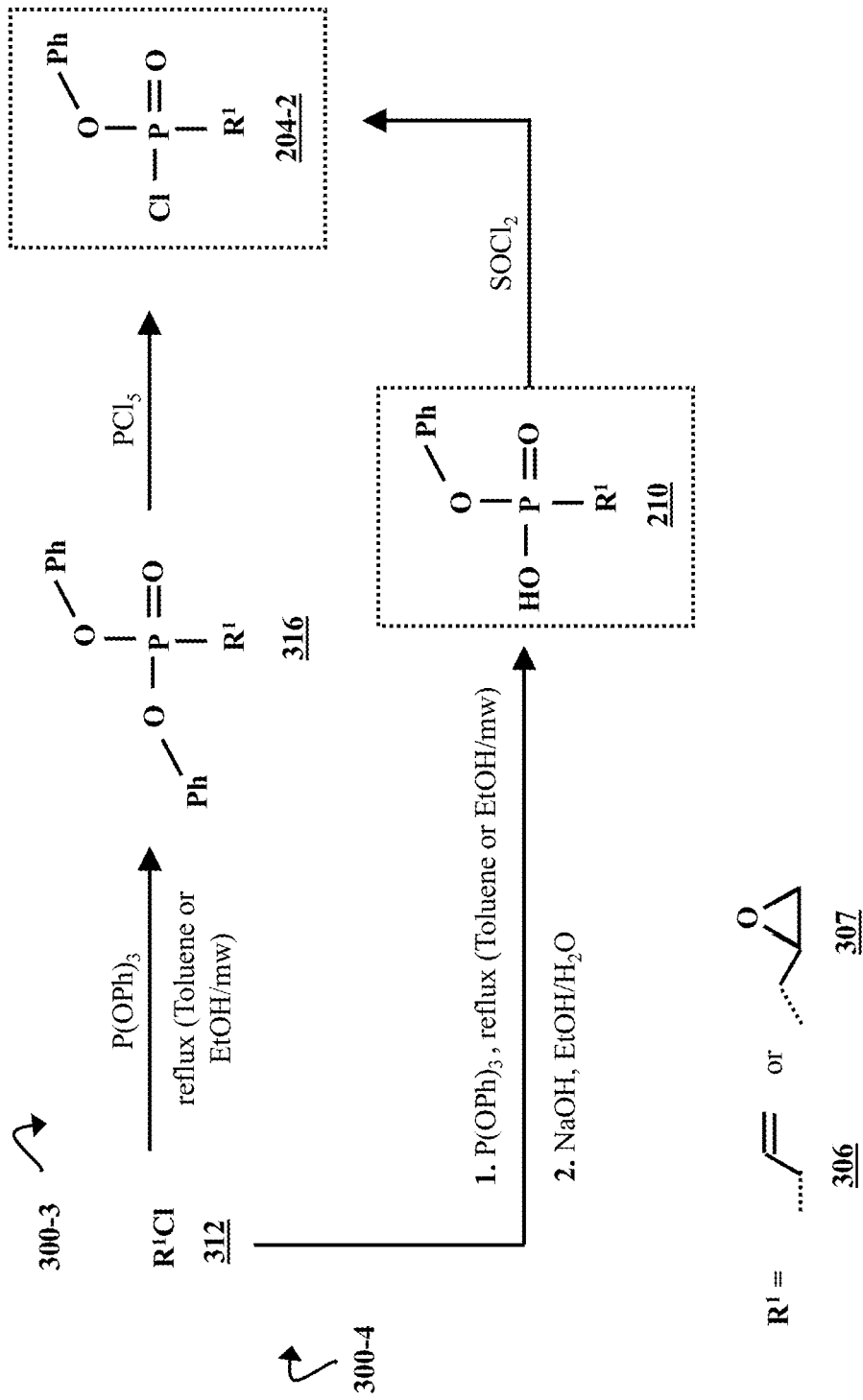
FIG. 3B is a chemical reaction diagram illustrating processes of forming two $R^1$-functionalized phosphonate-based compounds, according to some embodiments of the present disclosure.

FIG. 3B is a chemical reaction diagram illustrating processes 300-3 and 300-4 of forming two $R^1$-functionalized phosphonate-based compounds 204-2 and 210, according to some embodiments of the present disclosure. In both processes 300-3 and 300-4, an organochloride ($R^1Cl$) 312 is a starting material for the $R^1$-functionalized phosphonate-based compound 204-2. The organochloride has either an allyl $R^1$ group 306 or an epoxy $R^1$ group 307. It should be noted that, as in the case of the alcohol 304, organochlorides with chains of varying lengths (e.g., one to twelve methylene bridge groups) could be used. Additionally, organochlorides with acrylate substituents are used in some embodiments. In process 300-3, the organochloride 312 is reacted with triphenyl phosphite $(P(OPh)_3)$. The mixture is heated, either by refluxing in toluene or microwaving in ethanol (EtOH/mw), producing a phosphonyl ester precursor 316 to the $R^1$-functionalized phosphonate-based compound 204-2. The phosphonyl ester precursor 316 is reacted with phosphorus pentachloride $(PCl_5)$ to form the $R^1$-functionalized phosphonate-based compound 204-2.

In process 300-4, a mixture of the organochloride 312 and triphenyl phosphite $(P(OPh)_3)$ is heated, either by refluxing in toluene or microwaving in ethanol (EtOH/mw), forming a second $R^1$-functionalized phosphonate-based compound 210 which, in process 300-4, is a precursor to the first $R^1$-functionalized phosphonate-based compound 204-2. The reaction is then quenched by raising the pH of the solution. In this example, an ethanol/water $(EtOH/H_2O)$ solution of sodium hydroxide (NaOH) is added to the reaction mixture to quench the reaction. However, in some embodiments, bases other than NaOH, such as potassium hydroxide or lithium hydroxide, are used to quench the reaction. When the reaction has been quenched, thionyl chloride $(SOCl_2)$ is added to the phenylphosphinic acid precursor 210, producing the $R^1$-functionalized phosphonate-based compound 204-2.

Figure 3C:
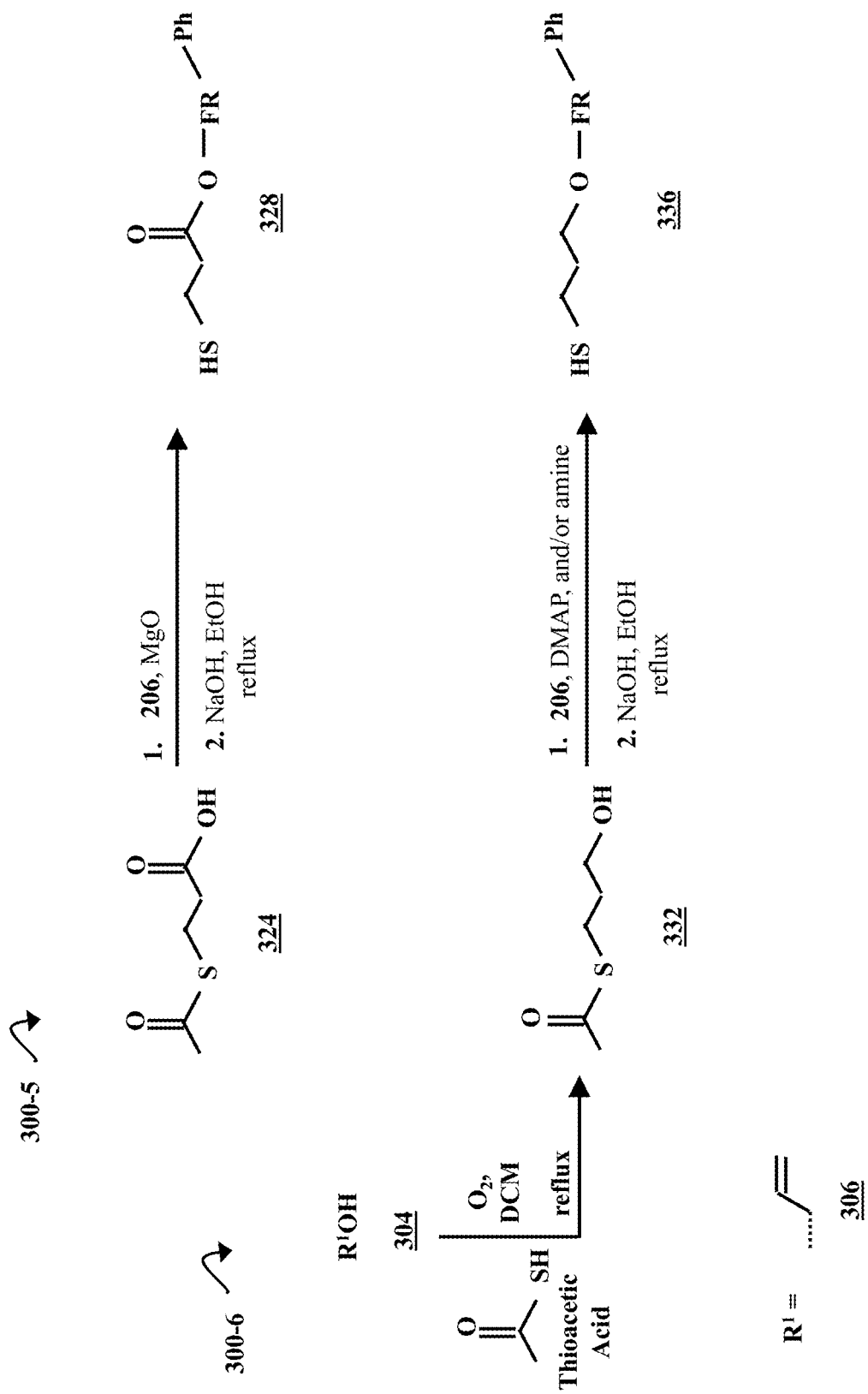
FIG. 3C is a chemical reaction diagram illustrating a process of forming a carboxylic acid-derived phenyl-substituted flame retardant thiol molecule and a process of forming a hydroxy-derived phenyl-substituted flame retardant thiol molecule, according to some embodiments of the present disclosure.

FIG. 3C is a chemical reaction diagram illustrating a process 300-5 of forming a carboxylic acid-derived phenyl-substituted flame retardant thiol molecule 328 and a process 300-6 of forming a hydroxy-derived phenyl-substituted flame retardant thiol molecule 336, according to some embodiments of the present disclosure. In process 300-5, acetate-protected thiopropionic acid 324 is reacted with magnesium oxide (MgO) and a phenyl-substituted phosphorus-based compound 206. The acetate group is then removed by refluxing the mixture in an ethanol (EtOH) solution containing NaOH, yielding the carboxylic acid-derived phenyl-substituted flame retardant thiol molecule 328.

In process 300-6, an alcohol ($R^1OH$) 304 with an allyl $R^1$ group 306 is reacted with thioacetic acid in a thiol-ene reaction. In the first step of the reaction, oxygen $(O_2)$ is added to a dichloromethane (DCM) solution of the allyl alcohol 304 and thioacetic acid. The mixture is refluxed, resulting in an acetate-protected mercaptopropanol 332. The second step in the reaction is a substitution reaction involving a phenyl-substituted phosphorus-based compound 206 and catalytic dimethylaminopyridine (cat. DMAP). It should be noted that the DMAP can be replaced by a stoichiometric amount of an organic amine, such as triethylamine. Additional examples of organic amines are discussed in greater detail with respect to FIG. 5A. The acetate group is removed by refluxing the mixture in an EtOH solution containing NaOH, leaving behind a terminal thiol group. This step results in the production of the hydroxy-derived phenyl-substituted flame retardant thiol molecule 336.

Figure 3D:
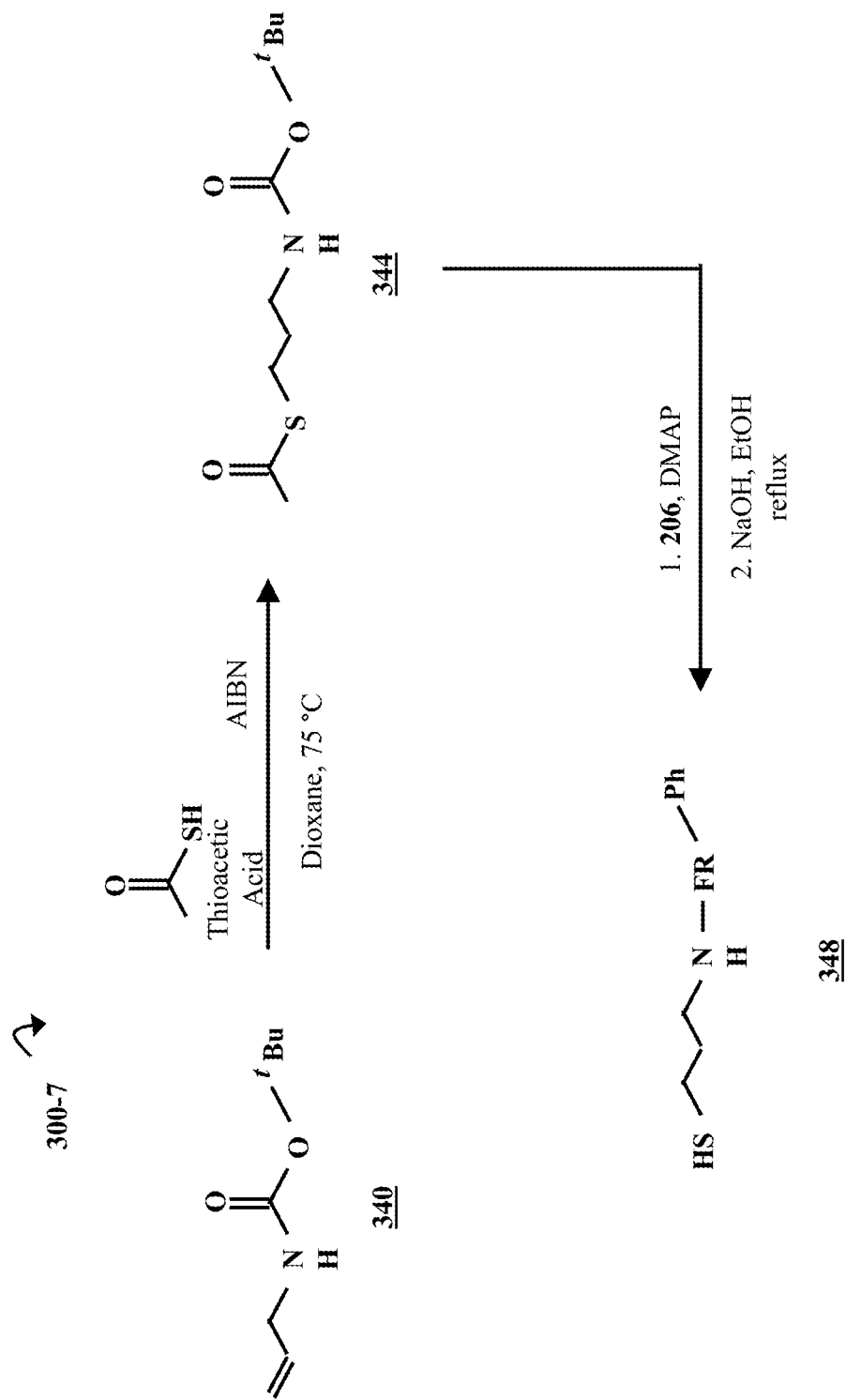
FIG. 3D is a chemical reaction diagram illustrating a process of forming an amine-derived phenyl-substituted flame retardant thiol molecule, according to some embodiments of the present disclosure.

FIG. 3D is a chemical reaction diagram illustrating a process 300-7 of forming an amine-derived phenyl-substituted flame retardant thiol molecule 348, according to some embodiments of the present disclosure. In process 300-7, 1-(boc-amino)-3-butene 340 is first reacted with thioacetic acid in a thiol-ene reaction. Azobisisobutyronitrile (AIBN) is added to the dioxane solution of 1-(boc-amino)-3-butene 340 and thioacetic acid, and the mixture is stirred at approximately 75° C., resulting in an acetate-protected precursor 344 to the amine-derived phenyl-substituted flame retardant thiol molecule 348. The second step in process 300-7 is a substitution reaction with a phenyl-substituted phosphorus-based compound 206 and cat. DMAP or a stoichiometric amount of an organic amine, such as triethylamine. The acetate group and boc groups are removed under basic conditions (e.g., by refluxing the mixture in an EtOH solution containing NaOH). This step results in the production of the amine-derived phenyl-substituted flame retardant thiol molecule 348.

Each of the thiol compounds 328, 336, and 348 produced in processes 300-5, 300-6, and 300-7 can provide a phenyl-substituted thioether-linked group in the formation of phenyl-substituted thioether-linked pinene-based flame retardant compounds. These reactions are discussed in greater detail with respect to FIG. 6A. If processes 300-5, 300-6, and 300-7 are carried out with the phenyl-substituted phosphorus-based flame retardant compound 206-1, the resulting phenyl-substituted flame retardant thiol molecules 328, 336, and 348 will have phosphoryl FR groups, and, if the reactions are carried out with 206-2, the resulting phenyl-substituted flame retardant thiol molecules 328, 336, and 348 will have phosphonyl FR groups. It should also be noted that processes 300-5, 300-6, and 300-7 can be carried out with the $R^1$-functionalized phosphorus-based flame retardants 204, resulting in thiol molecules with $R^1$ functional groups. These $R^1$ functional groups can participate in any of the reactions illustrated below that involve $R^1$ functional groups and their derivatives, though these reactions are not shown.

Figure 3E:
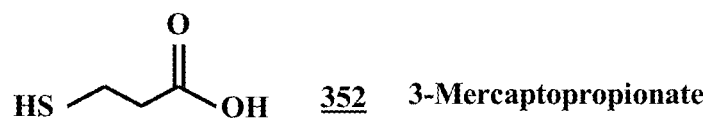
FIG. 3E is a diagrammatic representation of the molecular structures of three thiol molecules that are involved in the synthesis of pinene-based compounds, according to some embodiments of the present disclosure.
Figure 3E:
Figure 3E:
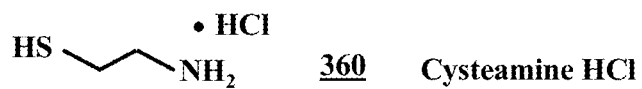

FIG. 3E is a diagrammatic representation 350 of the molecular structures of three thiol molecules 352, 356, and 360 that can be used in the synthesis of pinene-based flame retardant compounds, according to some embodiments of the present disclosure. The three thiol molecules are 3-mercaptopropionate 352, 2-mercaptoethanol 356, and cysteamine hydrochloride (HCl) 360. Each of these thiols provides a thioether moiety and a functional group (e.g., carboxylic acid, hydroxyl, or amino functional groups) in the synthesis of a functionalized thioether-linked pinene-based flame retardant compound. The syntheses and structures of the functionalized thioether-linked flame retardant pinene-derived compounds are discussed in greater detail with respect to FIG. 6B.

Figure 4A:
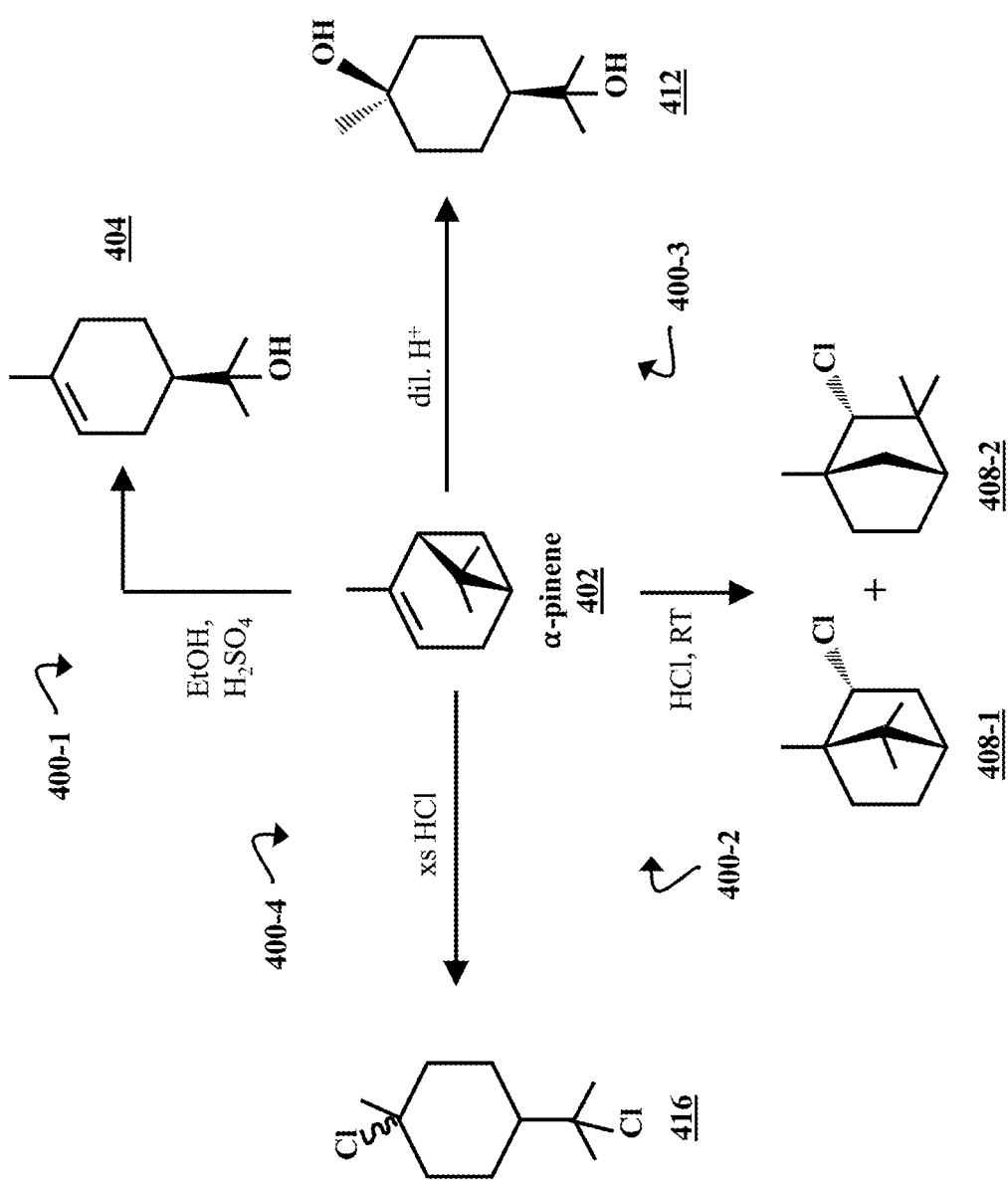
FIG. 4A is chemical reaction diagram illustrating processes of forming derivatives of $\alpha$-pinene, according to some embodiments of the present disclosure.

FIG. 4A is chemical reaction diagram illustrating processes 400-1, 400-2, 400-3, and 400-4 of forming four derivatives of α-pinene 402, according to some embodiments of the present disclosure. In process 400-1, α-pinene 402 is hydrogenated by addition of concentrated sulfuric acid $(H_2SO_4)$ in an EtOH solution, producing the α-pinene derivative (R)-2-(4-methylcyclohex-3-en-1yl)propan-2-ol 404 (referred to herein as terpineol 404). Concentrated $H_2SO_4$ refers to an approximately 18 moles per liter (M), or ~98% by mass, $H_2SO_4$ solution.

In process 400-2, α-pinene 402 is mono-chlorinated in a reaction with approximately one molar equivalent of hydrochloric acid (HCl). This reaction is carried out at room temperature (RT, e.g., 15-27° C.), and produces a mixture of bornyl chloride 408-1 and fenchyl chloride 408-2. Bornyl chloride 408-1 is the major product of this reaction. Therefore, the mixture is referred to and illustrated herein as bornyl chloride 408 for simplicity, though the mixture contains small amounts of fenchyl chloride 408-2. Additionally, it should be noted that reactions with the bornyl chloride/fenchyl chloride mixture 408 can produce mixtures of pinene-based flame retardant compounds with bornyl chloride cores and small amounts of pinene-based flame retardant compounds with fenchyl chloride cores. However, only the bornyl chloride cores are illustrated herein.

In process 400-3, α-pinene 402 is hydroxylated in a dilute acid solution (dil. $H^+$). Acids that can be added can include phosphoric acid ($H_3PO_4$), nitric acid ($HNO_3$), and hydrochloric acid (HCl). A dilute acid solution generally refers to an aqueous acid solution having a molarity that is less than approximately half the molarity of the concentrated acid. For example, concentrated HCl is approximately 12 M. Therefore, a dilute solution of HCl may be a solution with a concentration of HCl ranging between approximately 6 M and approximately 0.001 M. However, lower concentrations can be used. The dil. $H^+$ solution is slowly added (e.g., over a range of time between approximately 1 hour and approximately 6 hours) to α-pinene 402 while stirring at a low temperature (e.g., between approximately −10° C. and approximately 10° C.). The reaction is quenched by slowly adding the mixture to water at a temperature below approximately 25° C. This reaction 400-3 produces (1s,4s)-4-(2-hydroxypropan-2-yl)-1-methylcyclohexan-1-ol 412 (referred to herein as terpin 412).

In process 400-4, α-pinene 402 is reacted with excess hydrochloric acid (xs HCl) to produce achiral 1-chloro-4-(2-chloropropan-2-yl)-1-methylcyclohexane 416 (dichloro terpinene 416). The wavy line representing a chlorine-carbon bond in this structure illustrates the achirality of the bond. It should also be noted that the direction of bonds that provide chirality to structures are represented by black wedges and hatched wedges. This notation is known to persons of ordinary skill in the art.

Figure 4B:
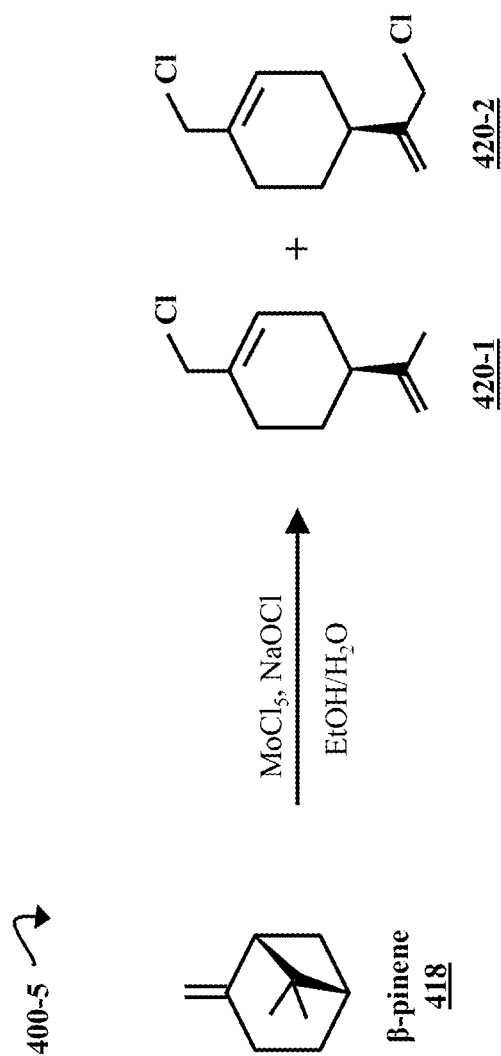
FIG. 4B is a chemical reaction diagram illustrating a process of forming derivatives of beta ($\beta$)-pinene, according to some embodiments of the present disclosure.

FIG. 4B is a chemical reaction diagram illustrating a process 400-5 of forming two derivatives 420-1 and 420-2 of β-pinene 418, according to some embodiments of the present disclosure. In process 400-5, β-pinene 418 is chlorinated with molybdenum chloride ($MoCl_5$) and sodium hypochlorite to give a mixture of (S)-1-(chloromethyl)-4-(prop-1-en-2-yl)cyclohex-1-ene 420-1 (referred to herein as mono-chloro limonene 420-1) and (S)-1-(chloromethyl)-4-(3-chloroprop-1-en-2-yl)cyclohex-1-ene 420-2 (referred to herein as di-chloro limonene 420-2), respectively. This mixture is referred to collectively herein as chloro limonene 420.

Figure 5A:
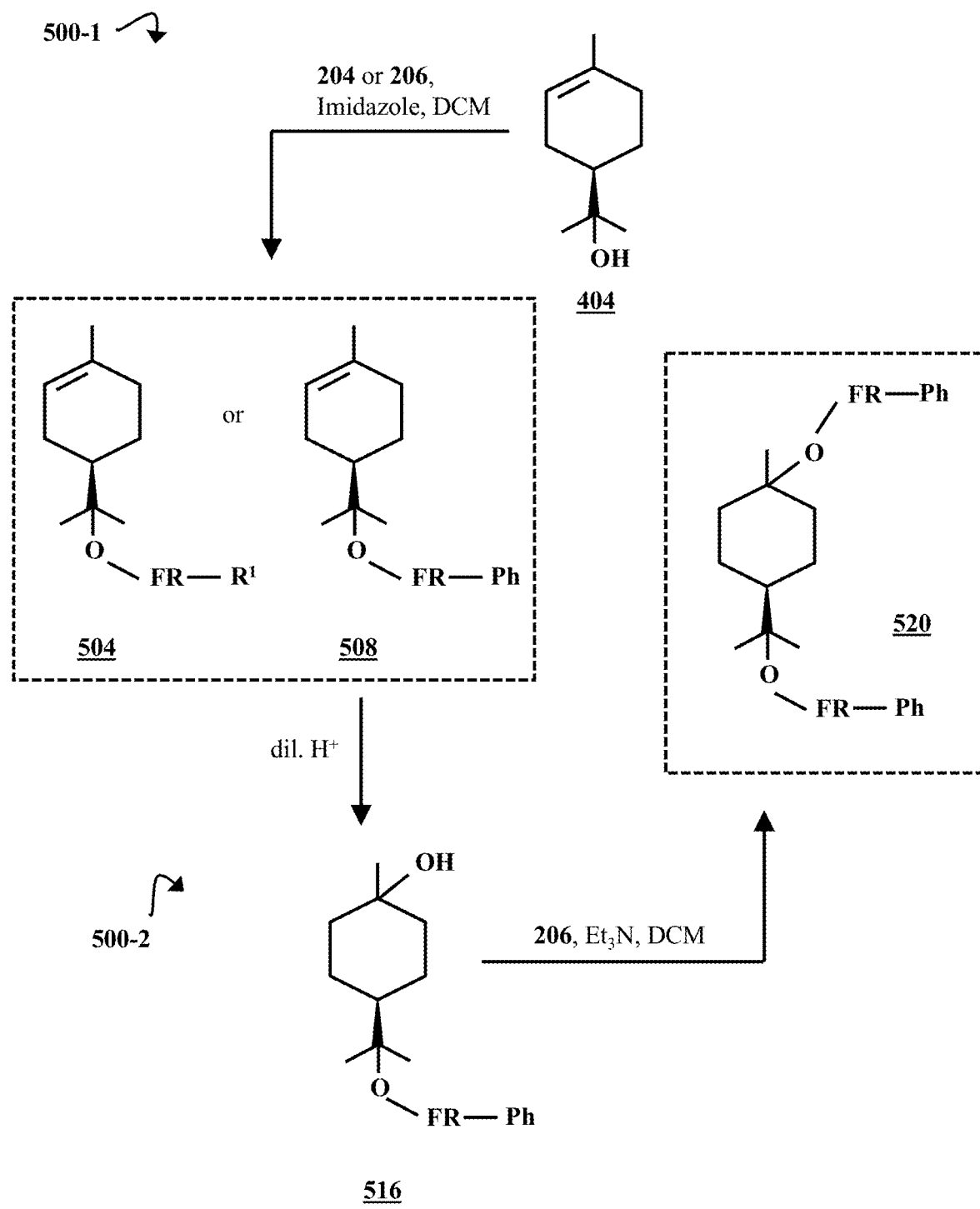
FIG. 5A is a first chemical reaction diagram illustrating processes of forming pinene-based flame retardant compounds from terpineol, according to some embodiments of the present disclosure.

FIG. 5A is a first chemical reaction diagram illustrating processes 500-1 and 500-2 of forming pinene-based flame retardant compounds 504, 508, and 520 from terpineol 404, according to some embodiments of the present disclosure. In process 500-1, terpineol 404 is reacted with a phosphorus-based flame-retardant compound 204 or 206 and a catalytic amount of imidazole in a dichloromethane (DCM) solution. In some embodiments, imidazole is replaced by another organic amine. Examples of organic amines that can be used can include dimethylaminopyridine (DMAP), trimethylamine, triethylamine ($Et_3N$), N,N-diisopropylethylamine, triphenylamine, and 1,8-diazabicyclo[5.4.0]undec-7-ene, etc. In some embodiments, the reaction is quenched by refluxing the mixture with sodium hydroxide (NaOH) in an EtOH solution. If an $R^1$-functionalized phosphorus-based compound 204 is used in the reaction, a mono-$R^1$-functionalized pinene-based flame retardant compound 504 is formed, and if a phenyl-substituted phosphorus-based compound 206 is used, a mono-phenyl-substituted pinene-based flame retardant compound 508 is formed.

In process 500-2, the mono-phenyl-substituted pinene-based flame retardant compound 508 is hydroxylated by addition of a dilute acid (dil. $H^+$) solution. This reaction can be carried out under substantially similar conditions to the hydroxylation reaction 400-3 discussed with respect to FIG. 4A. Examples of acids that can be used can include $HNO_3$, $H_3PO_4$, and HCl. This reaction produces a pinene-based flame-retardant compound having a phenyl substituent and a hydroxyl group 516. The hydroxylated compound 516 is then reacted in a DCM solution with a phenyl-substituted phosphorous-based flame retardant compound 206 and a catalytic amount of $Et_3N$, though other organic amines can be used. Examples of additional organic amines are discussed in greater detail above. This reaction produces a di-phenyl-substituted pinene-based flame retardant compound 520. Further, it should be noted that the hydroxylated compound 516 can be isolated and incorporated into a polymer to impart flame retardancy in some embodiments.

The reaction to form compound 520 can also be carried out with an $R^1$-functionalized phosphorus-based flame compound 204 to form a pinene-based flame retardant compound with one $R^1$-functionalized FR group and one phenyl-substituted FR group. It should also be noted that the steps illustrated in process 500-2 can be carried out with the mono-$R^1$-functionalized pinene-based flame retardant compound 504 to form analogous pinene-based flame retardant products (e.g., a pinene-based flame retardant compound having an $R^1$-functionalized FR group and a phenyl-substituted FR group or a pinene-based flame retardant compound having two $R^1$-functionalized FR groups), though these reactions are not illustrated herein.

Figure 5B:
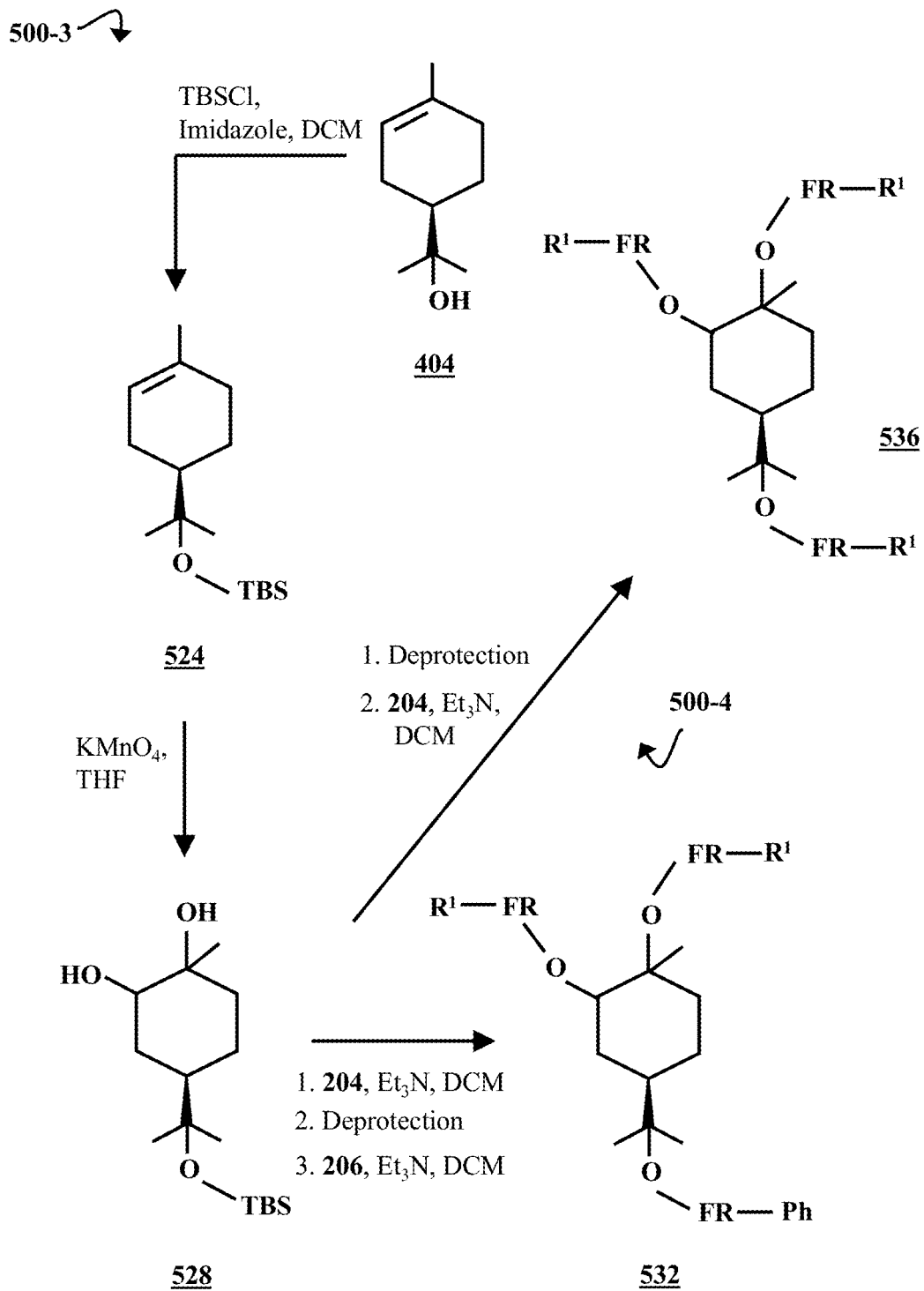
FIG. 5B is a second chemical reaction diagram illustrating processes of forming pinene-based flame retardant compounds from terpineol, according to some embodiments of the present disclosure.

FIG. 5B is a second chemical reaction diagram illustrating processes 500-3 and 500-4 of forming pinene-based flame retardant compounds 532 and 536 from terpineol 404, according to some embodiments of the present disclosure. In the first step of process 500-3, terpineol 404 is reacted with in a mixture of tert-butyldimethylsilyl chloride (TBSCl) and imidazole in DCM. This reaction attaches a TBS protecting group to the hydroxyl group on terpineol 404, forming a compound referred to herein as protected terpineol 524. In some embodiments, compounds other than TBSCl can be used to add alternative protecting groups (e.g., acetic anhydride ($Ac_2O$), tert-butyldimethylsilyl (TBDMS) ether, methoxymethyl (MOM) ether, tetrahydropyranyl (THP) ether, tert-butyl ether, allyl ether, benzyl ether (Bn-OR), tert-butyldiphenylsilyl (TBDPS) ether, benzoic acid ester, acetonide, and benzylidene acetal).

In the next step in process 500-3, the protected terpineol 524 is di-hydroxylated by potassium permanganate ($KMnO_4$) in THF. In some embodiments, $KMnO_4$ can be replaced by another oxidizing agent, such as osmium tetroxide ($OsO_4$). The di-hydroxylated protected terpineol compound 528 formed in this step is then reacted with an $R^1$-functionalized phosphorus-based compound 204 and $Et_3N$ (or another of the organic amines discussed above) in DCM. This step attaches two $R^1$-functionalized FR groups to the protected terpineol 524 to form a protected intermediate (not shown). A deprotection reaction is then carried out on the intermediate to remove the protecting group. The deprotection involves addition of an acid, such as HCl or p-toluenesulfonic acid, and is carried out using standard deprotecting techniques.

After deprotection, the deprotected terpineol intermediate is reacted with a phenyl-substituted phosphorus-based compound 206 and a stoichiometric amount of $Et_3N$ (or another of the organic amines discussed above) in DCM. This step adds a phenyl-substituted FR group at the newly exposed hydroxyl group location, forming a di-$R^1$-functionalized pinene-based flame retardant compound 532. However, in some embodiments, the phenyl-substituted phosphorus-based flame retardant compound 206 is used before deprotection, and the $R^1$-functionalized phosphorus-based flame retardant compound 204 after deprotection. This produces a mono-$R^1$-functionalized pinene-based flame retardant compound (not shown). Additionally, in some embodiments, the hydroxyl group can be left exposed without a second phosphorus-based compound reaction. This would produce a pinene-based flame retardant compound having a hydroxyl group (not shown).

Process 500-4 is an alternate reaction with the di-hydroxylated protected terpineol compound 528 formed in the second step of process 500-3. First, a deprotection reaction is carried out on the di-hydroxylated protected terpineol compound 528. Deprotection reactions are discussed in greater detail above. The deprotection reaction produces an intermediate compound having three hydroxyl groups (not shown). This intermediate is then reacted with an $R^1$-functionalized phosphorus-based compound 204 to form a tri-$R^1$-functionalized pinene-based flame retardant compound 536. This reaction is carried out in DCM in the presence of $Et_3N$ (or another of the organic amines discussed above). Additionally, process 500-4 can be carried out with a phenyl-substituted phosphorus-based compound 206 in some embodiments, producing a tri-phenyl-substituted pinene-based flame retardant compound (not shown).

Figure 5C:
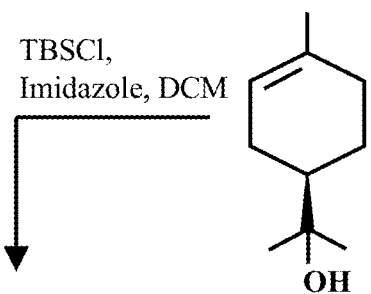
FIG. 5C is third a chemical reaction diagram illustrating a process of forming a pinene-based flame retardant compound from terpineol, according to some embodiments of the present disclosure.
Figure 5C:
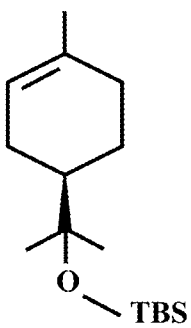
Figure 5C:
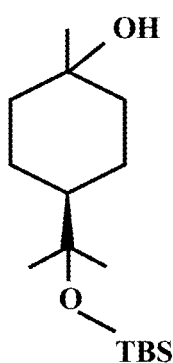
Figure 5C:
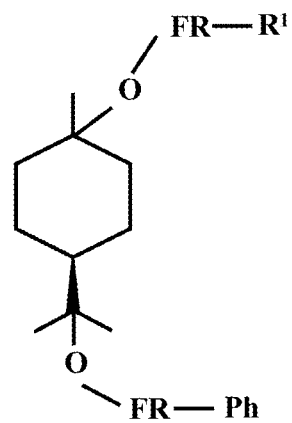

FIG. 5C is third a chemical reaction diagram illustrating a process 500-5 of forming a pinene-based flame retardant compound 548 from terpineol 404, according to some embodiments of the present disclosure. The first step in process 500-5 produces the protected terpineol compound 524 by reaction with TBSCl and imidazole in DCM. This reaction is discussed in greater detail with respect to FIG. 5B. The protected terpineol compound 524 is then hydroxylated by addition of a dilute acid (dil. $H^+$) solution to form a mono-hydroxylated protected terpineol compound 544. Hydroxylation with dil. $H^+$ solutions is discussed in greater detail with respect to FIG. 4A.

The next step in process 500-5 is carried out under substantially similar conditions to the reaction that converts compound 528 into compound 532 in FIG. 5B. That is, a reaction with an $R^1$-functionalized phosphorus-based compound 204 is followed by a deprotection step to remove the TBS protecting group. The compound is then reacted with a phenyl-substituted phosphorus-based compound 206 to form a mono-$R^1$-functionalized pinene-based flame retardant compound 548. It should be noted that the first and third steps in this reaction (i.e., reactions with 204 and 206, respectively) can be reversed to produce an alternative pinene-based flame retardant compound with the $R^1$ functional group and phenyl substituent in the opposite positions (not shown).

Figure 5D:
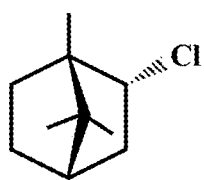
FIG. 5D is a chemical reaction diagram illustrating a process of forming pinene-based flame retardant compounds from bornyl chloride, according to some embodiments.
Figure 5D:
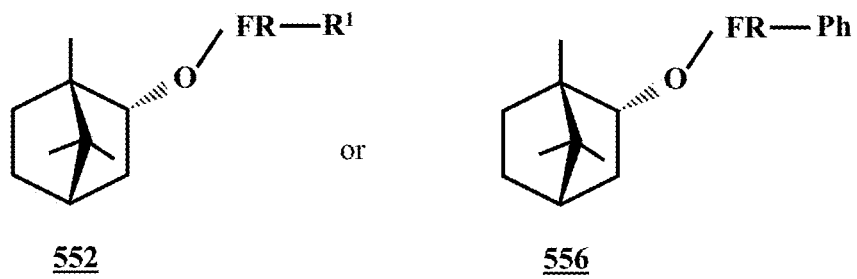

FIG. 5D is a chemical reaction diagram illustrating a process 500-6 of forming pinene-based flame retardant compounds 552 and 556 from bornyl chloride 408, according to some embodiments. In this reaction, bornyl chloride 408 is reacted with a phosphorus-based flame-retardant compound 208 or 210 and cesium carbonate ($Cs_2CO_3$) in a DMF solution. If an $R^1$-functionalized phosphorus-based compound 208 is used in the reaction, an $R^1$-functionalized pinene-based flame retardant compound 552 is formed, and if a phenyl-substituted phosphorus-based compound 210 is used, a phenyl-substituted pinene-based flame retardant compound 556 is formed.

Figure 5E:
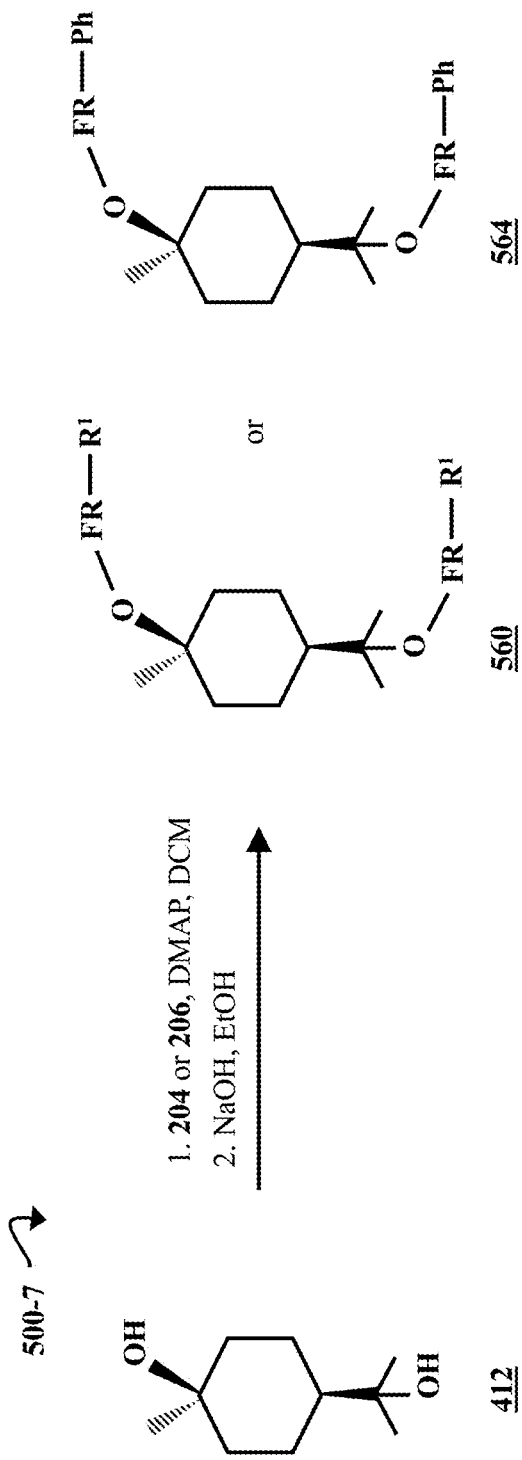
FIG. 5E is a chemical reaction diagram illustrating a process of forming pinene-based flame retardant compounds from terpin, according to some embodiments of the present disclosure.

FIG. 5E is a chemical reaction diagram illustrating a process 500-7 of forming pinene-based flame retardant compounds 560 and 564 from terpin 412, according to some embodiments of the present disclosure. In the first step of process 500-7, terpin 412 is reacted with a phosphorus-based flame retardant compound 204 or 206 and a catalytic amount of DMAP (or another of the organic amines discussed above) in DCM. In the second step, the reaction is quenched by addition of NaOH in EtOH. If an $R^1$-functionalized phosphorus-based compound 204 is used in the reaction, a di-$R^1$-functionalized pinene-based flame retardant compound 560 is formed, and if a phenyl-substituted phosphorus-based compound 206 is used, a di-phenyl-substituted pinene-based flame retardant compound 564 is formed.

Figure 5F:
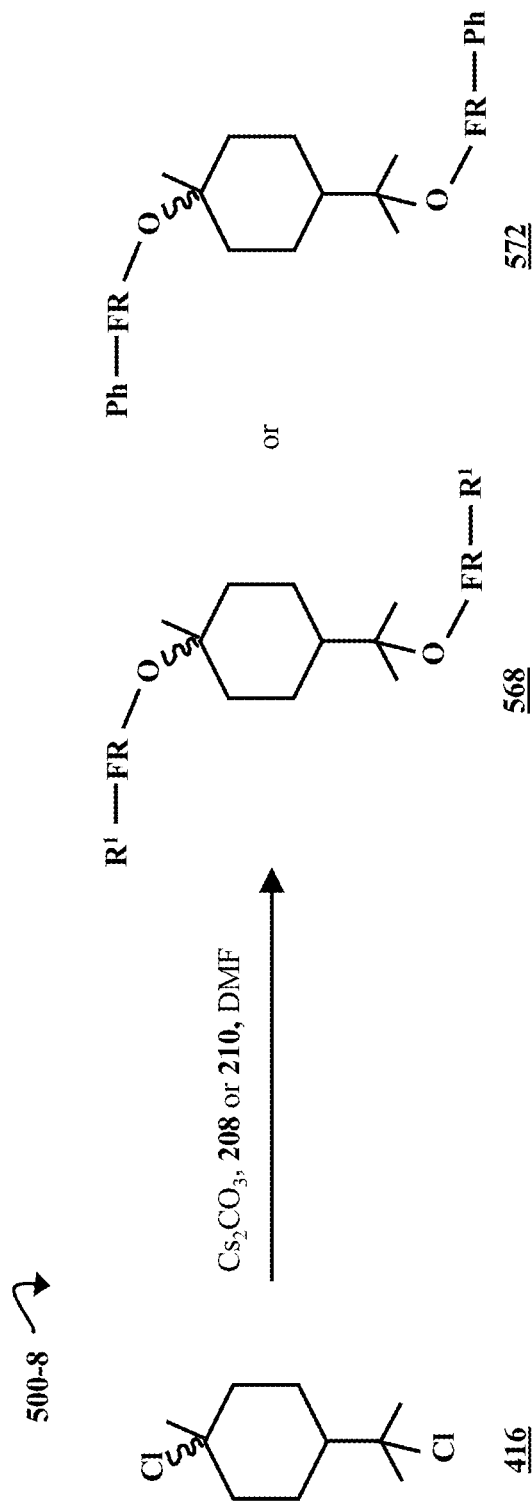
FIG. 5F is a chemical reaction diagram illustrating a process of forming pinene-based flame retardant compounds from dichloro terpinene, according to some embodiments of the present disclosure.

FIG. 5F is a chemical reaction diagram illustrating a process 500-8 of forming pinene-based flame retardant compounds 568 and 572 from dichloro terpinene 416, according to some embodiments of the present disclosure. In this reaction, dichloro terpinene 416 is reacted with a phosphorus-based flame-retardant compound 208 or 210 and $Cs_2CO_3$ in a DMF solution. If an $R^1$-functionalized phosphorus-based compound 208 is used in the reaction, a di-$R^1$-functionalized pinene-based flame retardant compound 568 is formed, and if a phenyl-substituted phosphorus-based compound 210 is used, a di-phenyl-substituted pinene-based flame retardant compound 572 is formed.

Figure 5G:
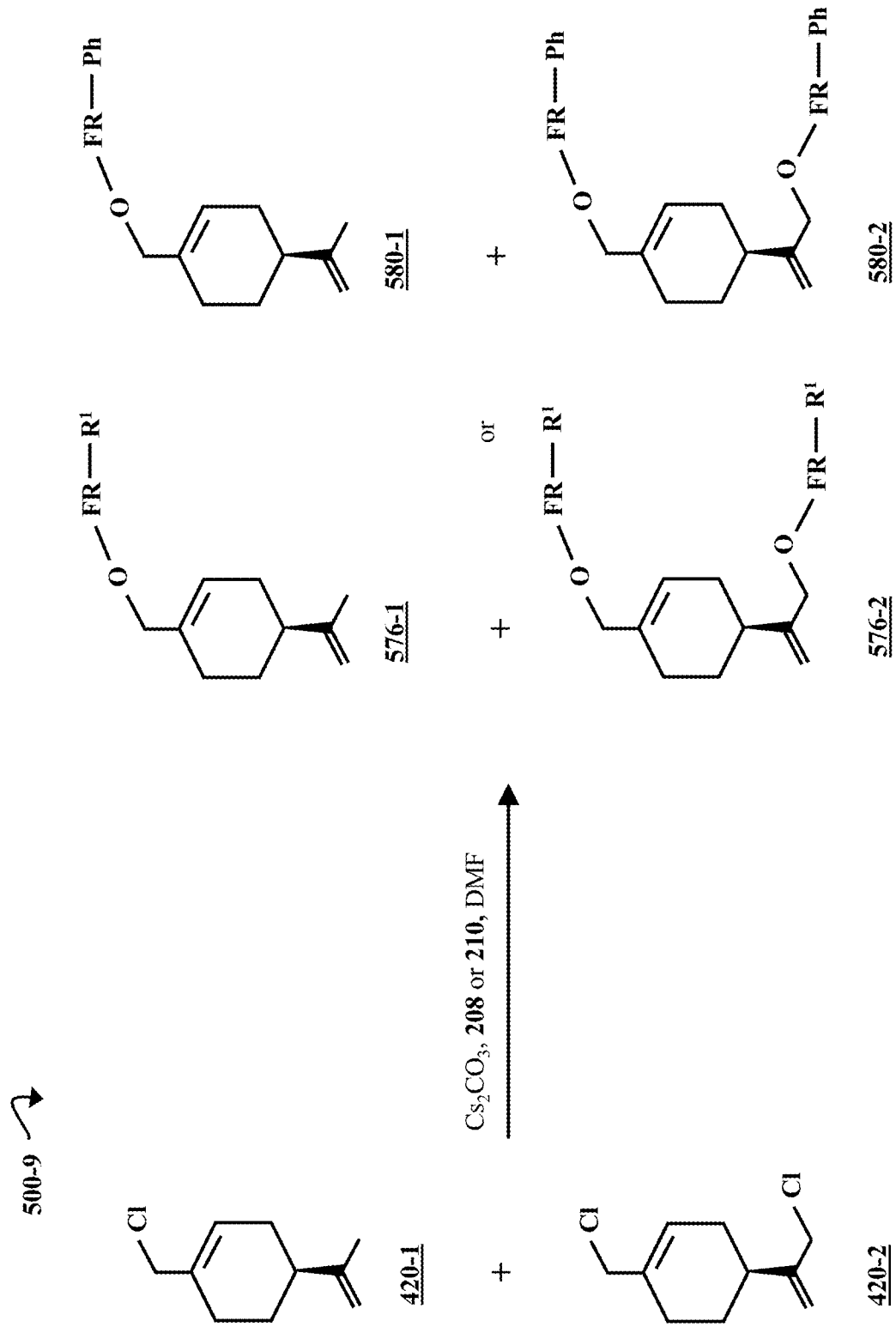
FIG. 5G is a chemical reaction diagram illustrating a process of forming pinene-based flame retardant compounds from a mixture of mono- and di-chloro limonene, according to some embodiments of the present disclosure.

FIG. 5G is a chemical reaction diagram illustrating a process 500-9 of forming pinene-based flame retardant compounds from a mixture of mono- and di-chloro limonene 420, according to some embodiments of the present disclosure. The chloro limonene 420 mixture is reacted with a phosphorus-based flame retardant compound 208 or 210 and $Cs_2CO_3$ in a dimethylformamide (DMF) solution. If an $R^1$-functionalized phosphorus-based flame retardant compound 208 is used, a mixture of limonene-derived mono-576-1 and di-$R^1$-functionalized 576-2 pinene-based flame retardant compounds (referred to collectively as 576) are produced. However, if a phenyl-substituted phosphorus-based flame retardant compound 210 is used, a mixture of limonene-derived mono-580-1 and di-$R^1$-functionalized 580-2 pinene-based flame retardant compounds (referred to collectively as 580) are produced.

Figure 6A:
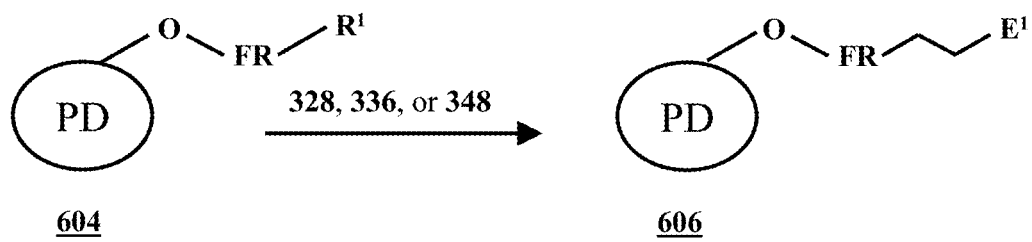
FIG. 6A is a chemical reaction diagram illustrating a process of converting a generic $R^1$-functionalized pinene-based flame retardant compound having an allyl $R^1$ group to a generic phenyl-substituted thioether-linked pinene-based flame retardant compound, according to some embodiments of the present disclosure.
Figure 6A:
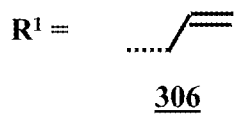
Figure 6A:
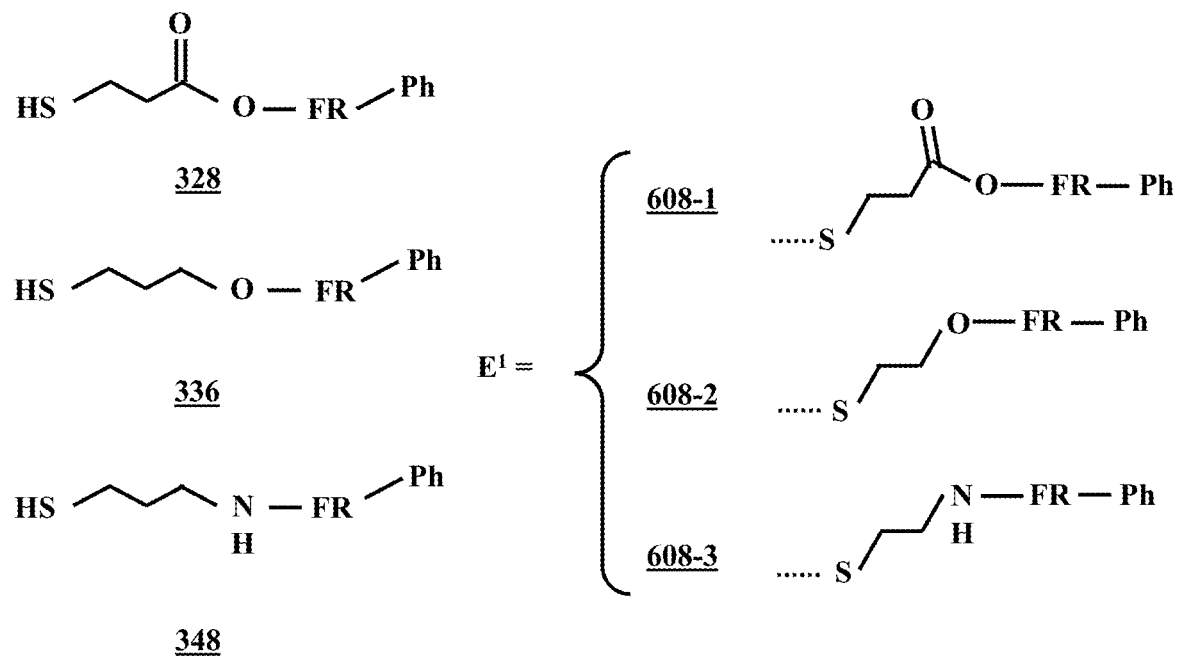

FIG. 6A is a chemical reaction diagram illustrating a process 600-1 of converting a generic $R^1$-functionalized pinene-based flame retardant compound 604 having at least one allyl $R^1$ group 306 to a generic phenyl-substituted thioether-linked pinene-based flame retardant compound 606, according to some embodiments of the present disclosure. The phenyl-substituted thioether-linked groups are referred to as $E^1$ groups 608-1, 608-2, and 608-3 (collectively, 608) herein, and are bound at the FR moiety on the pinene-based flame retardant compound 606. The generic $R^1$-functionalized pinene-based flame retardant compound 604 is illustrated as having one FR group wherein $R^1$ is an allyl moiety 306. The pinene-based core of the molecule is illustrated by an oval labeled "PD." This oval represents the structure of the entire molecule, apart from the illustrated single FR group having a terminal allylic $R^1$ group 306, for any $R^1$-functionalized pinene-based flame retardant compounds discussed herein (e.g., 504, 532, 536, 548, 552, 568, 567-1, 580-1, etc.).

Process 600-1 is a thiol-ene reaction between the generic $R^1$-functionalized pinene-based flame retardant compound 604 having allyl $R^1$ group 306 and a phenyl-substituted flame retardant thiol compound 328, 336, or 348. The syntheses and structures of these phenyl-substituted flame retardant thiol compounds are discussed in greater detail with regard to FIGS. 3C and 3D. The thiol compounds react with the allyl $R^1$ group 306 on the generic $R^1$-functionalized pinene-based flame-retardant compound 604. It should be noted that the thiol compounds will react with any allyl $R^1$ groups 306 bound to a pinene-based flame retardant compound. For example, if the compound represented by the generic compound 604 is a tri-$R^1$-functionalized compound (e.g., compound 536), the resulting $E^1$ thioether-linked compound represented by generic compound 606 will have three thioether-linked substituents.

The thiol-ene reaction of process 600-1 can be carried out under a variety of conditions. For example, when process 600-1 includes the carboxylic acid-derived flame retardant thiol compound 328, the reaction is carried out under ultraviolet (UV) light in a methanol (MeOH) solution. Additionally, when process 600-1 includes the hydroxy-derived flame retardant thiol compound 336, the reaction is carried out under UV light. Further, when process 600-1 includes the amine-derived flame retardant thiol compound 348, the reaction is carried out under UV light in an approximately pH 9 methanol solution. The $E^1$ thioether-linked compounds formed in process 600-1, and represented by generic compound 606, can be blended with polymers to form a flame retardant polymeric material.

Figure 6B:
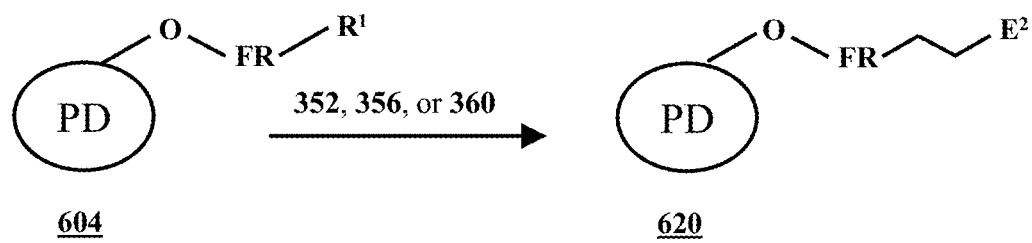
FIG. 6B is a chemical reaction diagram illustrating a process of converting the generic $R^1$-functionalized pinene-based flame retardant compound to a generic functionalized thioether-linked pinene-based flame retardant compound, according to some embodiments of the present disclosure.
Figure 6B:
Figure 6B:
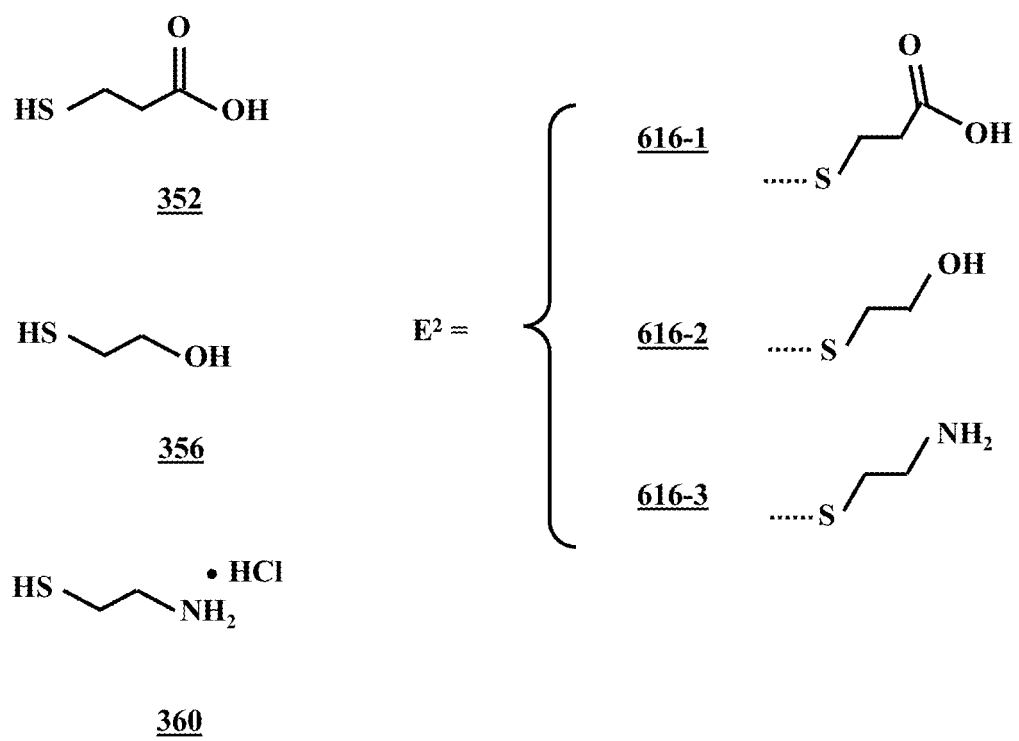

FIG. 6B is a chemical reaction diagram illustrating a process 600-2 of converting the generic $R^1$-functionalized pinene-based flame retardant compound 604 to a generic functionalized thioether-linked pinene-based flame retardant compound 620, according to some embodiments of the present disclosure. The functionalized thioether-linked groups are referred to as $E^2$ groups 616-1, 616-2, and 616-3 (collectively, 616) herein, and are bound to the FR moiety on the pinene-based flame retardant compound 620. The generic $R^1$-functionalized pinene-based flame retardant compound 604 is discussed in greater detail with respect to FIG. 6A.

Process 600-2 is a thiol-ene reaction between the generic $R^1$-functionalized pinene-based flame retardant compound 604 having allyl $R^1$ group 306 and a thiol compound. Thiol compounds 3-mercaptopropionate 352, 2-mercaptoethanol 356, and cysteamine HCl 360 are illustrated herein. However, alternative thiol compounds can be used, as would be understood by a person of ordinary skill in the art. The thiol compounds react with the allyl $R^1$ group 306 on the generic $R^1$-functionalized pinene-based flame-retardant compound 604. Further, it should be noted that thiol compounds will react with any allyl $R^1$ groups 306 bound to a pinene-based flame retardant compound. For example, if the compound represented by the generic compound 604 is a tri-$R^1$-functionalized compound (e.g., compound 536), the resulting $E^2$ thioether-linked compound represented by generic compound 606 will have three thioether-linked groups.

The thiol-ene reaction of process 600-2 can be carried out under a variety of conditions. For example, when process 600-2 includes mercaptopropionate 352, the reaction is carried out under ultraviolet (UV) light in a methanol (MeOH) solution. Additionally, when process 600-2 includes 2-mercaptoethanol, the reaction is carried out under UV light. Further, when process 600-2 includes cysteamine HCl 360, the reaction is carried out under UV light in an approximately pH 9 methanol solution. The $E^2$ thioether-linked compounds 620 formed in process 600-2 can be blended with, or bound to, polymers to form a flame retardant polymeric material. In some embodiments, these flame retardant compounds 620 can act as cross-linkers.

Figure 6C:
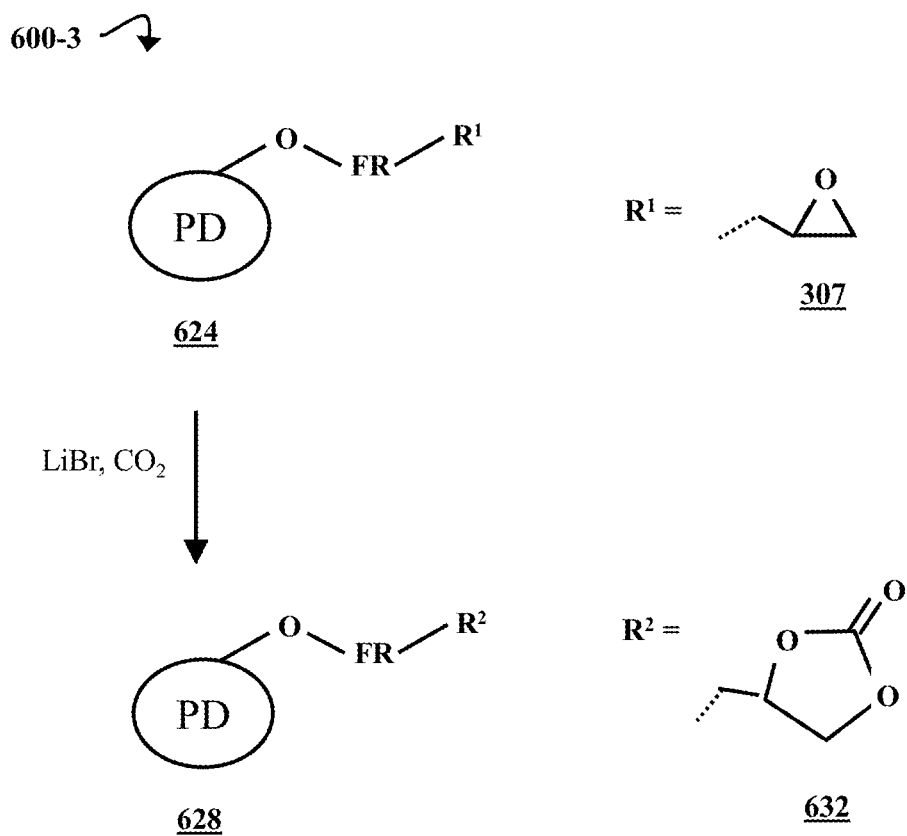
FIG. 6C is a chemical reaction diagram illustrating a process of converting a generic $R^1$ pinene-based flame retardant compound having an epoxy $R^1$ group to a generic propylene carbonate $R^2$-functionalized pinene-based flame retardant compound, according to some embodiments of the present disclosure.

FIG. 6C is a chemical reaction diagram illustrating a process 600-3 of converting a generic $R^1$ pinene-based flame retardant compound 624 having an epoxy $R^1$ group 307 to a generic propylene carbonate $R^2$-functionalized pinene-based flame retardant compound 628, according to some embodiments of the present disclosure. Other than the identity of the $R^1$ groups, the generic $R^1$-functionalized pinene-based flame retardant compound 624 having the epoxy $R^1$ group 307 is substantially the same as the generic $R^1$-functionalized pinene-based flame retardant compound 604 having an allyl $R^1$ group 306. The structure of the generic compounds is discussed in greater detail with respect to FIG. 6A.

In process 600-3, the generic $R^1$-functionalized pinene-based flame retardant compound 624 is combined with lithium bromide (LiBr) in an appropriate solvent (e.g., methanol, ethanol, ether, acetone, etc.). Carbon dioxide ($CO_2$) is added to the mixture, either by bubbling or by injecting into the headspace of a flask containing the mixture. The $CO_2$ reacts with the epoxy $R^1$ groups 307 to produce a pinene-based flame retardant compound 628 having a propylene carbonate $R^2$ functional group 632. A propylene carbonate $R^2$ functional group can be formed in a LiBr/$CO_2$ reaction with any of the pinene-based flame retardant compounds having epoxy $R^1$ functional groups discussed herein.

Figure 7A:
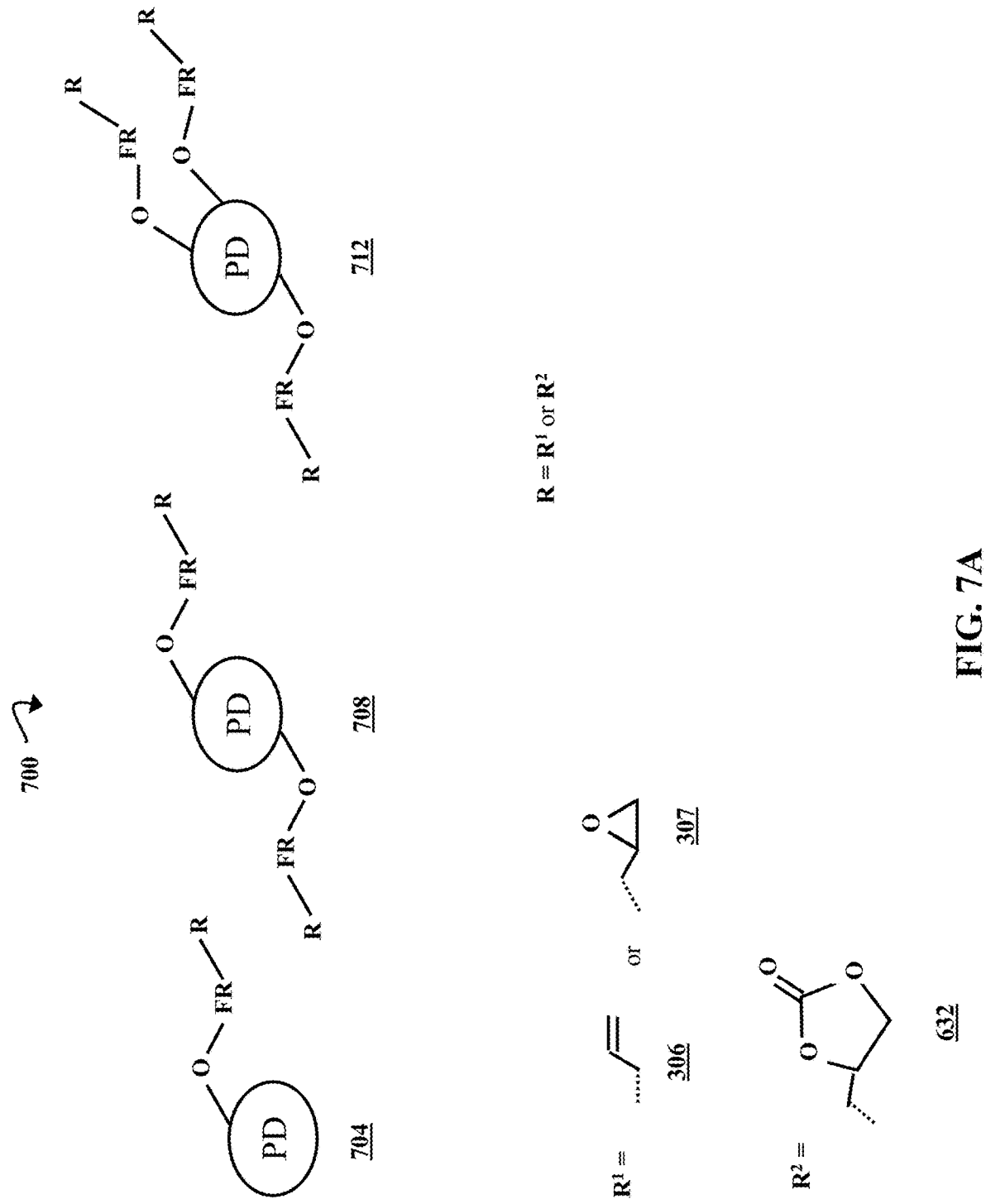
FIG. 7A is a diagrammatic representation of the structures of generic R-functionalized pinene-based flame retardant monomers according to some embodiments of the present disclosure.

FIG. 7A is a diagrammatic representation of the structures 700 of generic R-functionalized pinene-based flame retardant monomers 704, 708, and 712 according to some embodiments of the present disclosure. In FIG. 7A, R can refer to an $R^1$ group or an $R^2$ group. The generic monomers represent mono-R-functionalized pinene-based flame retardant monomers 704 (e.g., compounds 504, 548, 552, 576-1, etc.), di-R-functionalized pinene-based flame retardant monomers 708 (e.g., 532, 560, 568, 576-2, etc.), and tri-R-functionalized pinene-based flame retardant monomers 712 (e.g., compound 536). For simplicity, each structure in FIG. 7A shows only ligands with R functional groups (allyl 306, epoxy 307, or propylene carbonate 632). An oval labeled "PD" represents the pinene derivative core of each monomer. The functionalized pinene-based flame retardant monomers 704, 708, and 712 are polymerized to form pinene-based flame retardant polymers.

Figure 7B:
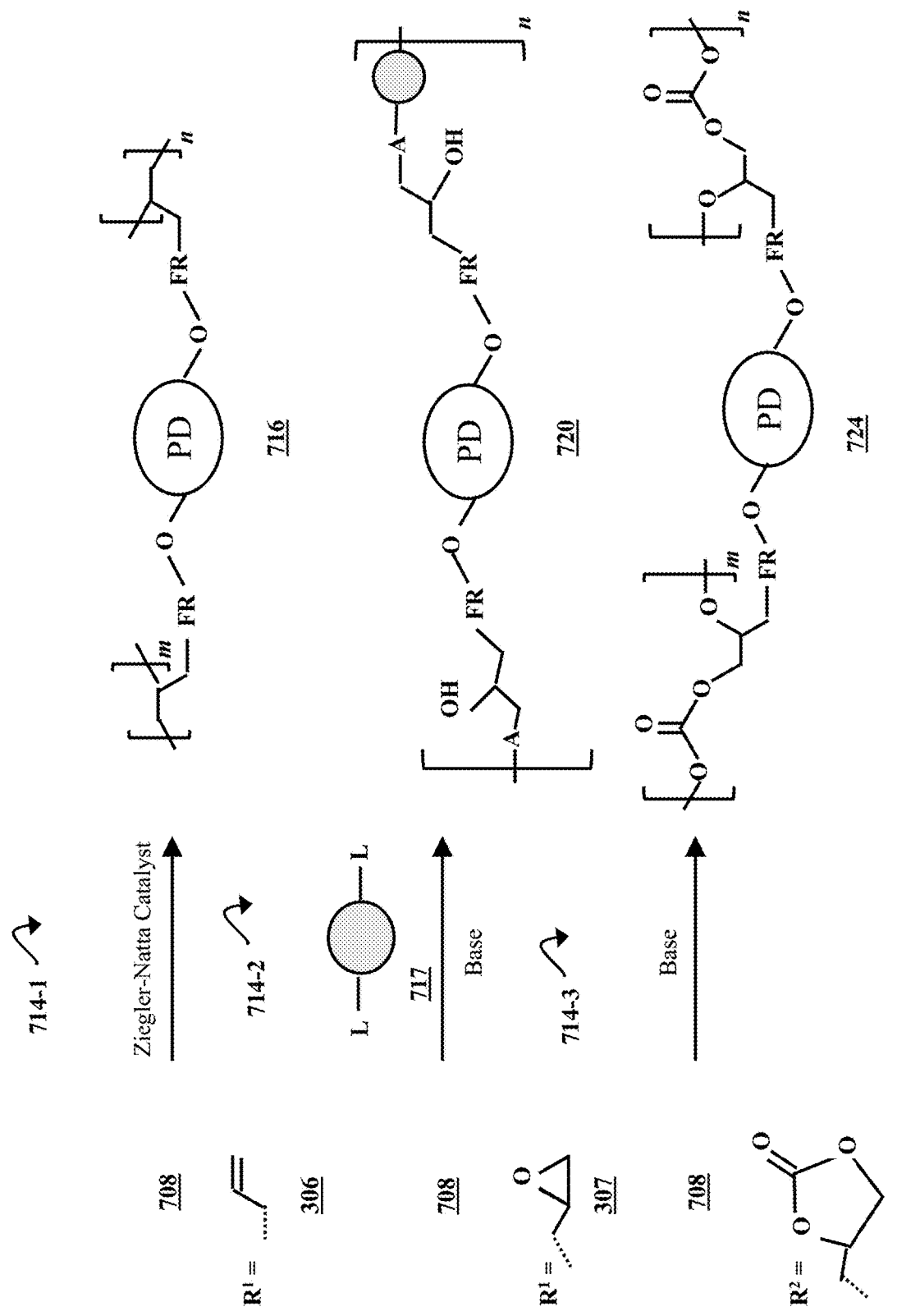
FIG. 7B is a chemical reaction diagram illustrating processes of forming pinene-based flame retardant polymers from pinene-based flame retardant compounds, according to some embodiments of the present disclosure.

FIG. 7B is a chemical reaction diagram illustrating processes 714-1, 714-2, and 714-3 of forming pinene-based flame retardant polymers 716, 720, and 724 from pinene-based flame retardant compounds 708, according to some embodiments of the present disclosure. The polymers illustrated herein are examples of polymers that can be synthesized from the pinene-based flame retardant compounds, but other polymers can be produced as well (e.g., by changing reaction conditions, co-monomers, R groups, etc.). Processes 714-1-714-3 illustrate the polymerization of difunctionalized pinene-based flame retardant monomers 708 only. However, it should be noted that processes 714-1 and 714-3 can also be carried out with the mono-R-functionalized pinene-based flame retardant monomers 704, and processes 714-1-714-3 can be carried out with the tri-R-functionalized pinene-based flame retardant monomers 712. Further, in some embodiments, the polymerization reactions are carried out with a mixture of monomers 704, 708, and/or 712.

In process 714-1, allyl-derived pinene-based flame retardant polymers 716 are formed from di-R-functionalized pinene-based flame retardant monomer 708 having allyl $R^1$ groups 306. The di-R-functionalized pinene-based flame retardant monomer 708 is reacted with a Ziegler-Natta catalyst. Ziegler-Natta catalysts catalyze the polymerization of 1-alkenes. Examples of these catalysts can include heterogeneous Ziegler-Natta catalysts based on titanium compounds and homogeneous Ziegler-Natta catalysts based on complexes of titanium, zirconium, or hafnium. Heterogeneous and homogeneous Ziegler-Natta catalysts can be used in combination with organoaluminum co-catalysts in some embodiments.

In process 714-2, epoxy-derived pinene-based flame retardant polymers 720 are formed from di-R-functionalized pinene-based flame retardant monomer 708 having epoxy $R^1$ functional groups 307. This di-R-functionalized pinene-based flame retardant monomer 708 is reacted with a base and a second monomer 717. The second monomer 717 is a compound with at least two hydroxyl (—OH) groups or at least two amino (—NH$_2$) groups (e.g., a diol, polyol, diamine, polyamine, etc.) This monomer 717 is illustrated as a gray oval with attached L groups, which represent hydroxyl groups or amino groups. It should be noted that, while two L groups are illustrated herein, there are more than two L groups in some embodiments. Additionally, in some embodiments, the di-R-functionalized pinene-based monomer 708 having epoxy $R^1$ functional groups 307 self-polymerizes under basic conditions. In these instances, the reaction does not include the second monomer 717.

In process 714-3, propylene carbonate-derived pinene-based flame retardant polymers 724 are formed from di-R-functionalized pinene-based flame retardant monomers 708 having propylene carbonate $R^2$ functional groups 632. The di-R-functionalized pinene-based flame retardant monomer 708 is reacted in a ring-opening polymerization initiated by a base. Examples of bases that can be used as initiators can include NaOH, potassium hydroxide (KOH), lithium hydroxide (LiOH), 1,8-diazabicyclo[5.4.0]undec-7-ene (DBU), triazabicyclodecene (TBD), etc.

In addition to the polymers illustrated in FIG. 7B, the pinene-based flame retardant compounds disclosed herein can be used in the synthesis of other flame retardant polymers in some embodiments. An array of classes of flame retardant polymers can be made with different combinations of monomers. These polymerization processes are in accordance with polymer chemistry platforms that can include polyhydroxyurethanes, polycarbonates, polymers obtained by radical polymerization, polyurethanes, polyesters, polyacrylates, epoxy resins, polyimides, polyureas, polyamides, poly(vinyl-esters), etc.

The phenyl-substituted pinene-based flame retardant compounds having no $R^1$, $R^2$, or $E^2$ groups (e.g., compounds 508, 520, 556, 564, 572, 580, 606, etc.) are not polymerized or bound to polymers. This is because the phenyl (or other alkyl) substituent is relatively unreactive. However, these phenyl-substituted pinene-based flame retardant compounds can be blended with another polymer to form a flame retardant pinene-based polymer. Examples of these polymers can include polyurethanes, polyesters, polyacrylates, epoxy resins, polyimides, polyureas, polyamides, and poly(vinyl-esters). However, any other appropriate polymer or material can be used.

In some embodiments, additional compounds and materials are incorporated into the pinene-based flame retardant polymers. For example, cross-linkers and chain-extenders can be added to the polymerization reaction mixture. Examples of compounds that can be used as cross-linkers or chain-extenders can include ethylene glycol, di- or triethylene glycol, propylene glycol, di- or tripropylene glycol, 1,3-propanediol, 1,3- or 1,4-butanediol, neopenyl glycol, 1,6-hexanediol, 1,4-cyclohexanedimethanol, hydroquinone bis(2-hydroxyethyl) ether, ethanolamine, di- or triethanolamine, methyldiethanolamine, phenyldiethanolamine, glycerol, trimethylolpropane, 1,2,6-hexanetriol, pentaerythritol, N,N,N',N'-tetrakis-(2-hydroxypropyl)ethylenediamine; diethyl-toluenediamine, dimethyl-thio-toluenediamine, etc.

Additional examples of additives can include blowing agents (e.g., carbon dioxide (CO$_2$), pentane, hydrazine, 1,1,1,2-tetrafluoroethane, 1,1,1,3,3-pentafluoropropane, etc.), inorganic pigments (e.g., titanium dioxide, iron oxide yellow, nickel titanates, chrome titanates, chrome yellow, cadmium yellow, iron oxide brown, iron oxide red, cadmium red, iron/manganese mixed metal oxide black, iron oxide black, carbon black, mixed metal oxide blue, chrome oxide green, etc.), organic pigments (e.g., phthalocyanine blue, phthalocyanine green, perylene red, quinacridone red, monoazo yellow, isoindoline yellow, monoaryide yellow, etc.), additional flame retardants (e.g., phosphorus-based organic compounds, halogen-containing compounds, phosphorus-based inorganic compounds, etc.), surfactants (e.g., polydimethylsiloxane-polyoxyalkylene block copolymers, silicone oils, nonylphenol ethoxylates, etc.), fillers (e.g., plaster, glass microspheres, talc, marble dust, sand, ground limestone, bronze powder, fibers, etc.), smoke suppressants (e.g., trialkyl phosphate, ferrocene, tin compounds, etc.), plasticizers (e.g., diisooctyl phthalate, organophosphates, glycols/polyethers, polymeric plasticizers, adipates, sebacates, maleates, trimellitates, di- or tricarboxylic ester-based plasticizers, etc.), etc.

One example of an application of pinene-based flame retardant polymers or polymers that incorporate pinene-based flame retardant compounds is in plastics used in electronics hardware, such as integrated circuit packages. Additional applications can include acoustic dampening, cushioning, plastics, synthetic fibers, insulation, etc. The pinene-based flame retardant compounds can also be used to make adhesives such as bio-adhesives, elastomers, thermoplastics, emulsions, thermosets, etc. Further, materials containing the pinene-based flame retardant compounds can be incorporated into various devices with electronic components that can include printed circuit boards (PCBs), semiconductors, transistors, optoelectronics, capacitors, resistors, chip carriers, etc.

Resins for printed circuit boards (PCBs) can be made flame retardant by incorporating polymers that include pinene-based flame retardant compounds. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Using polymers that incorporate the pinene-based flame retardant compounds can prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are not to be construed as limiting. One skilled in the art would recognize that a variety of synthetic reactions may be used that vary in reaction conditions, components, methods, etc., which ultimately generate one or both of pinene-based flame retardant compounds and their corresponding polymer derivatives. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A pinene-based flame retardant compound, comprising:
a pinene derivative core; and
at least one flame retardant substituent, wherein the at least one flame retardant substituent includes a phosphorus-based moiety having a formula selected from a group consisting of

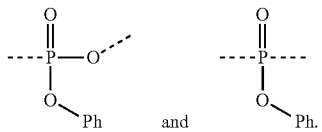

2. The pinene-based flame retardant compound of claim 1, wherein the pinene-based flame retardant compound has a formula selected from a group consisting of:

3. The pinene-based flame retardant compound of claim 1, wherein the pinene-based flame retardant compound has a formula selected from a group consisting of:

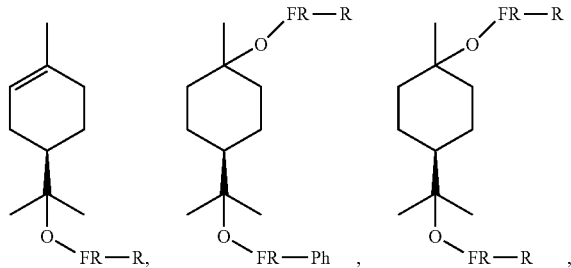

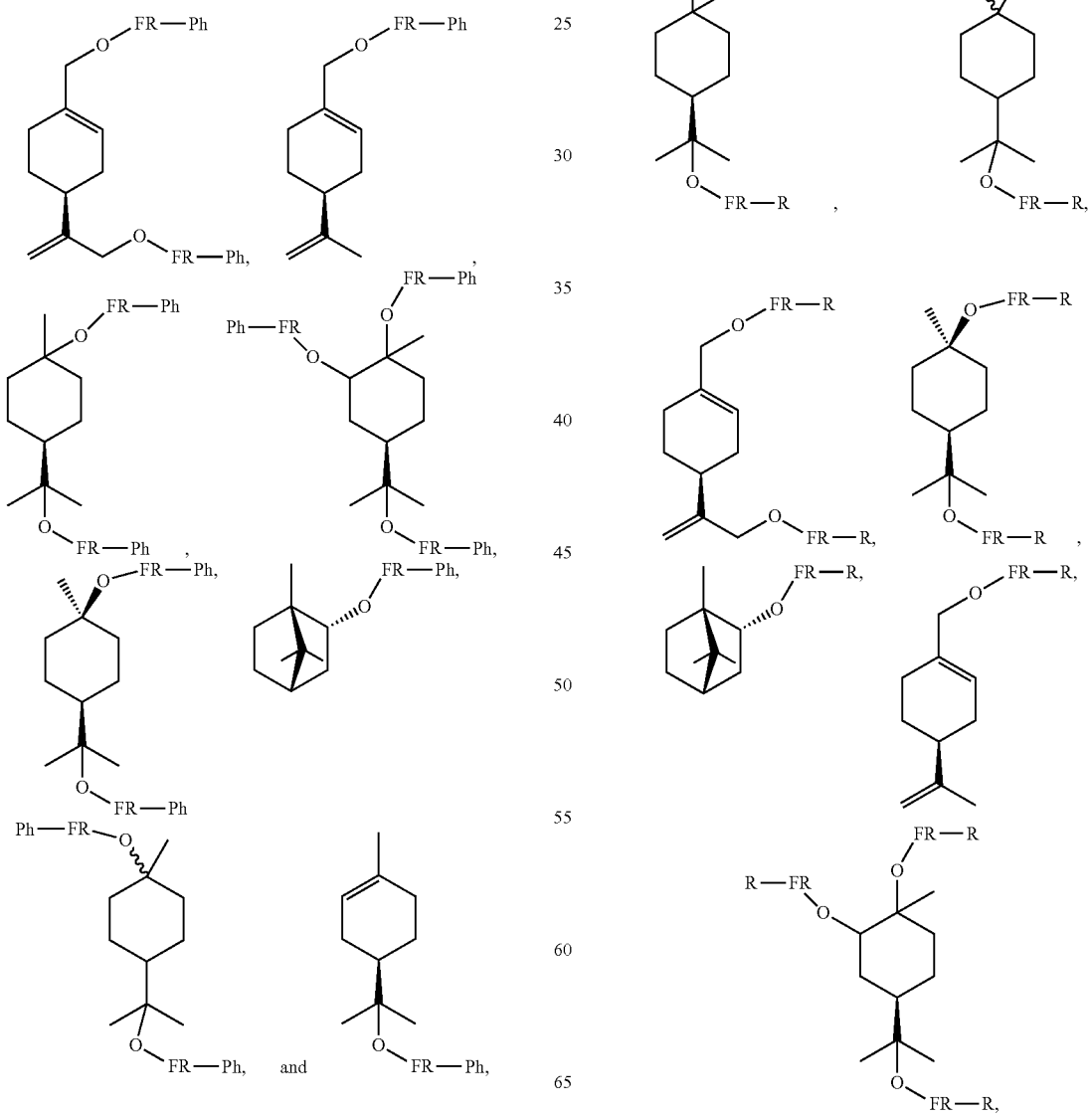

wherein FR is the phosphorus-based moiety.

-continued

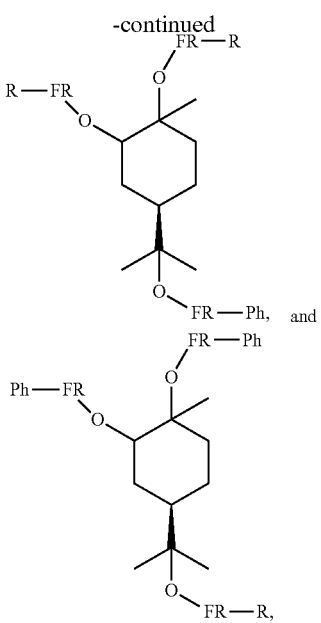

wherein FR is the phosphorus-based moiety and R is a functional group.

4. The pinene-based flame retardant compound of claim 3, wherein the R functional group is selected from a group consisting of an allyl group, an epoxy group, and a propylene carbonate group.

5. The pinene-based flame retardant compound of claim 1, wherein the pinene-based flame retardant compound is derived from pinene obtained from a bio-based source.

6. The pinene-based flame retardant compound of claim 1, wherein the pinene-based flame retardant compound includes a thioether-linked group.

7. The pinene-based flame retardant compound of claim 6, wherein the thioether-linked group has a formula selected from a group consisting of:

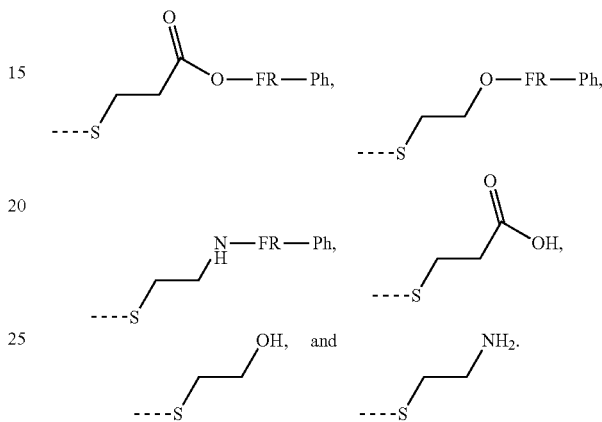

* * * * *